United States Patent
Zheleznyak et al.

(10) Patent No.: US 11,369,515 B2
(45) Date of Patent: Jun. 28, 2022

(54) VISION CORRECTION WITH LASER REFRACTIVE INDEX CHANGES

(71) Applicants: University of Rochester, Rochester, NY (US); Clerio Vision, Inc., Rochester, NY (US)

(72) Inventors: Leonard Zheleznyak, Pittsford, NY (US); Cory Leeson, Rochester, NY (US); Jonathan D. Ellis, Tucson, AZ (US); Theodore Foos, Mendon, NY (US); Sam C. Butler, Rochester, NY (US)

(73) Assignees: University of Rochester, Rochester, NY (US); Clerio Vision, Inc., Rochester, NY (US)

( * ) Notice: Subject to any disclaimer, the term of this patent is extended or adjusted under 35 U.S.C. 154(b) by 0 days.

(21) Appl. No.: 16/412,265

(22) Filed: May 14, 2019

(65) Prior Publication Data
US 2019/0343683 A1    Nov. 14, 2019

Related U.S. Application Data

(60) Provisional application No. 62/671,363, filed on May 14, 2018.

(51) Int. Cl.
   *A61F 9/008*    (2006.01)

(52) U.S. Cl.
   CPC ...... *A61F 9/00804* (2013.01); *A61F 9/00812* (2013.01); *A61F 9/00827* (2013.01); *A61F 2009/0088* (2013.01); *A61F 2009/00872* (2013.01); *A61F 2009/00897* (2013.01)

(58) Field of Classification Search
   CPC .............. A61F 9/00804; A61F 9/00812; A61F 9/00814; A61F 9/00806; A61F 9/00808
   See application file for complete search history.

(56) References Cited

U.S. PATENT DOCUMENTS

| | | |
|---|---|---|
| 5,849,006 A | 12/1998 | Frey et al. |
| 6,261,220 B1 | 7/2001 | Frey et al. |
| 6,270,221 B1 | 8/2001 | Liang et al. |
| 6,271,914 B1 | 8/2001 | Frey et al. |
| 6,830,332 B2 | 12/2004 | Piers et al. |
| 8,512,320 B1 * | 8/2013 | Knox ................. A61F 9/00829 606/5 |
| 9,545,340 B1 | 1/2017 | Knox et al. |

(Continued)

FOREIGN PATENT DOCUMENTS

WO    20150006274 A1    1/2015

OTHER PUBLICATIONS

U.S. Patent and Trademark Office (ISA/US), International Search Report and Written Opinion (ISR/WO) from International Patent Application No. PCT/US2019/032291, dated Jul. 18, 2019 (dated Sep. 20, 2019.).

(Continued)

*Primary Examiner* — Nathan J Jenness
*Assistant Examiner* — Skylar Lindsey Christianson
(74) *Attorney, Agent, or Firm* — Andrew J. Anderson, Esq.; Harter Secrest & Emery LLP

(57) ABSTRACT

Methods and systems wherein laser induced refractive index changes by focused femtosecond laser pulses in optical polymeric materials or ocular tissues is performed to address various types of vision correction.

22 Claims, 15 Drawing Sheets

(56) References Cited

U.S. PATENT DOCUMENTS

| | | |
|---|---|---|
| 2006/0256284 A1 | 11/2006 | Dahi et al. |
| 2008/0001320 A1* | 1/2008 | Knox .................. A61F 9/008 264/1.37 |
| 2008/0319428 A1* | 12/2008 | Wiechmann ........ A61F 9/00838 606/5 |
| 2009/0287306 A1 | 11/2009 | Smith et al. |
| 2011/0071509 A1* | 3/2011 | Knox .................. A61F 9/00829 606/5 |
| 2012/0078240 A1* | 3/2012 | Spooner .............. A61F 9/00827 606/5 |
| 2012/0310223 A1* | 12/2012 | Knox .................. A61F 9/00834 606/5 |
| 2012/0310340 A1 | 12/2012 | Knox et al. |
| 2013/0103144 A1 | 4/2013 | Bille |
| 2013/0338650 A1 | 12/2013 | Jester et al. |
| 2017/0156931 A1 | 6/2017 | Knox et al. |
| 2018/0243082 A1* | 8/2018 | Zheleznyak .......... A61F 2/1613 |

OTHER PUBLICATIONS

G.A. Gandara-Montano, et al., 'Femtosecond Laser Writing of Freeform Gradient Index Microlenses in Hydrogel-Based Contact Lenses', The Institute of Optics, University of Rochester, Optical Materials Express 2257, vol. 5, No. 10, Oct. 2015 DOI: 10.1364/OME.5.002257.

K. Wozniak et al., Scattering Properties of Ultrafast Laser-Induced Refractive Index Shaping Lenticular Structures in Hydrogels, SPIEDigitalLibrary.org/conference-proceedings-of-spie. Event: SPIE LASE, 2018, San Francisco, California, US. Downloaded from https://www.spiedigitallibrary.org/conference-proceedings-of-spie on Jul. 17, 2019.

* cited by examiner

*Figure 4. Conventional (left) and saturated (right) Fresnel lenses shown in cross-section with equal height of 300mW.*
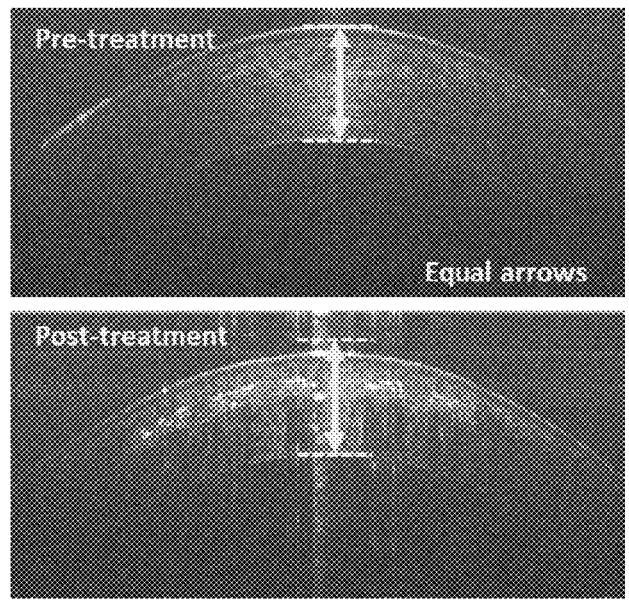
*Figure 5. OCT image of the same cat cornea before and after treatment. Note the decrease in corneal thickness.*

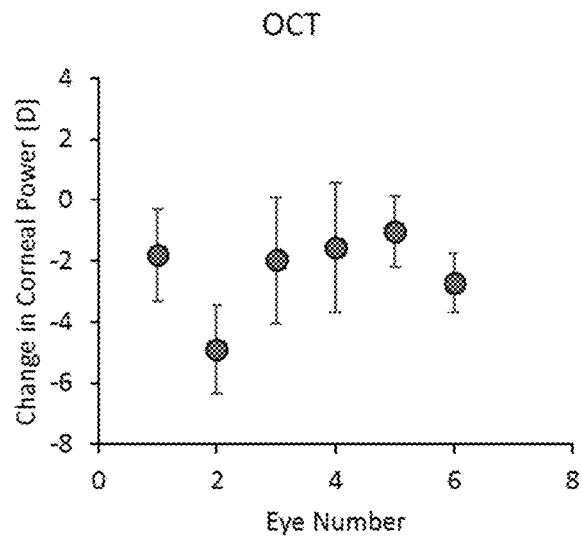
*Figure 6. Change in anterior corneal curvature [diopters] for 6 cat eyes before and after laser treatment measured with optical coherence tomography (OCT).*
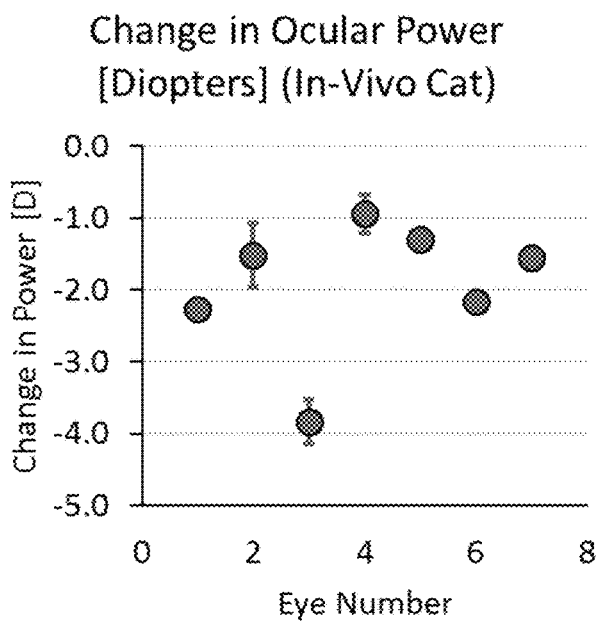
*Figure 7. Change in ocular aberrations for 7 cat eyes before and after laser treatment, measured over a 4.5mm diameter optical zone with a Shack-Hartmann wavefront sensor.*

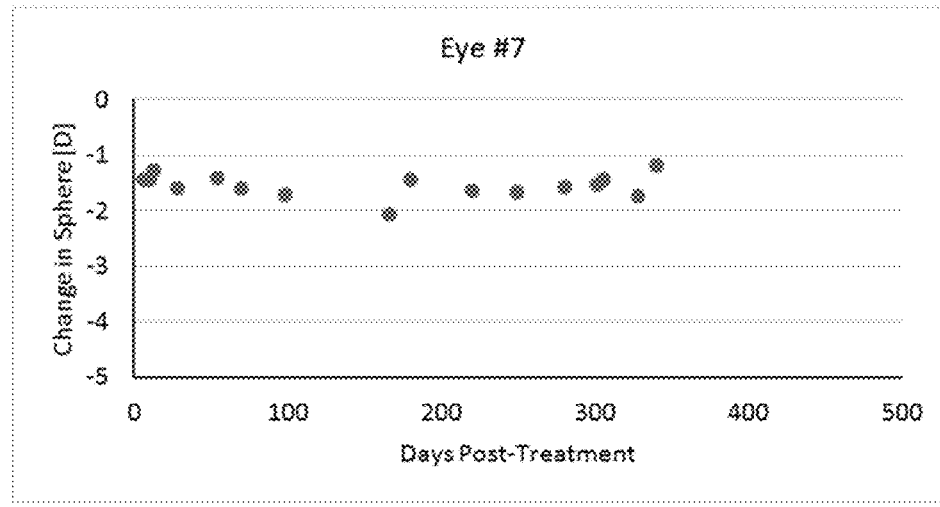
Figure 8. Change in ocular power over time after the laser treatment in one cat eye (#7).
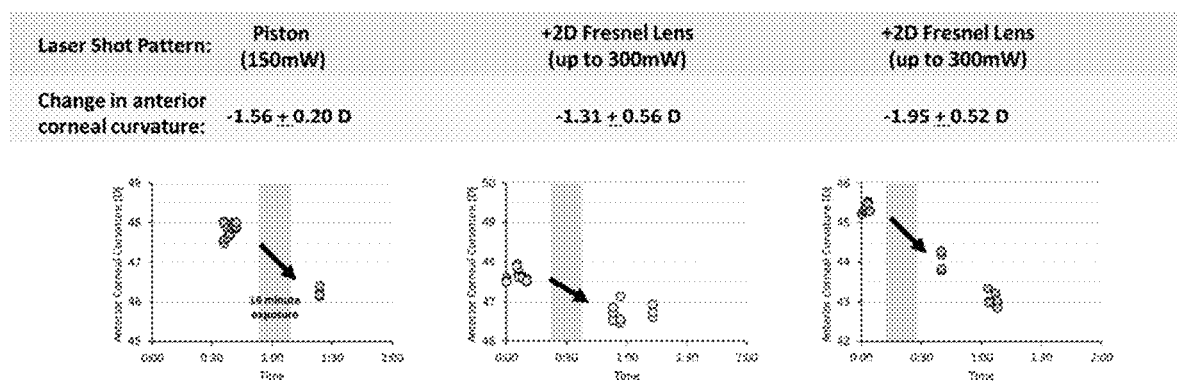
Figure 9. Results of ex-vivo rabbit eye experiments for Rabbit Eyes 5 (left), 6 (center) and 8 (right).

Method to measure and adjust ex-vivo IOP
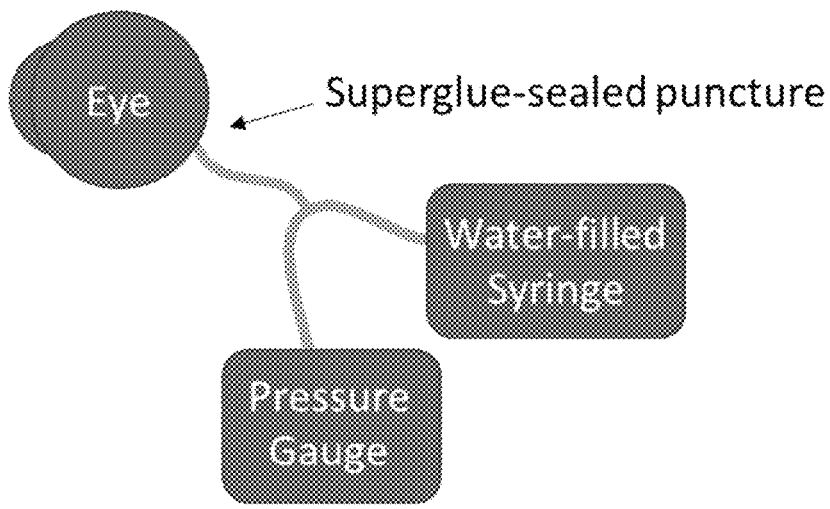
Figure 10. Apparatus for controlling and monitoring ocular pressure of ex-vivo rabbit eyes.
Impact of fs-laser treatment
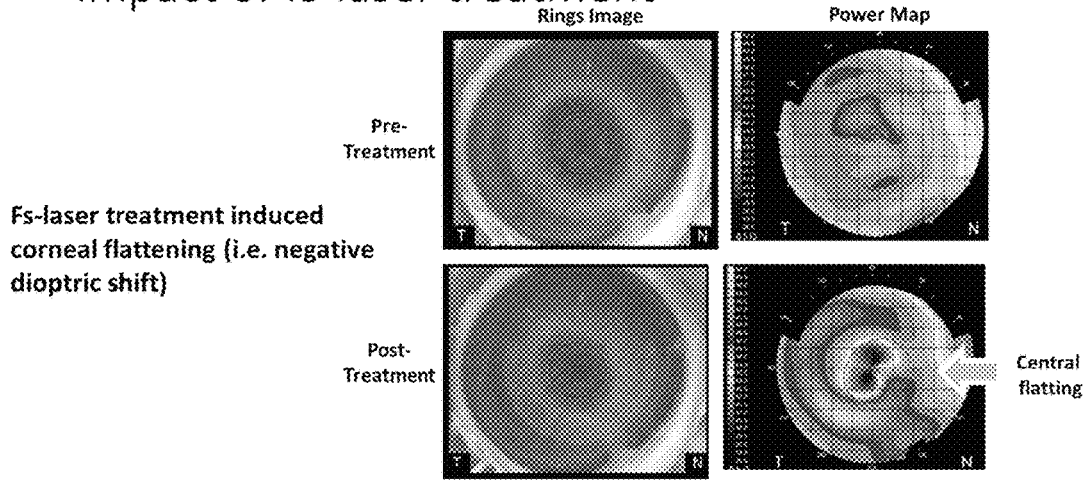
Figure 11. Corneal topography showing a central flattening of an ex-vivo rabbit cornea following fs-laser treatment. A central flattening corresponds to a myopia correction.

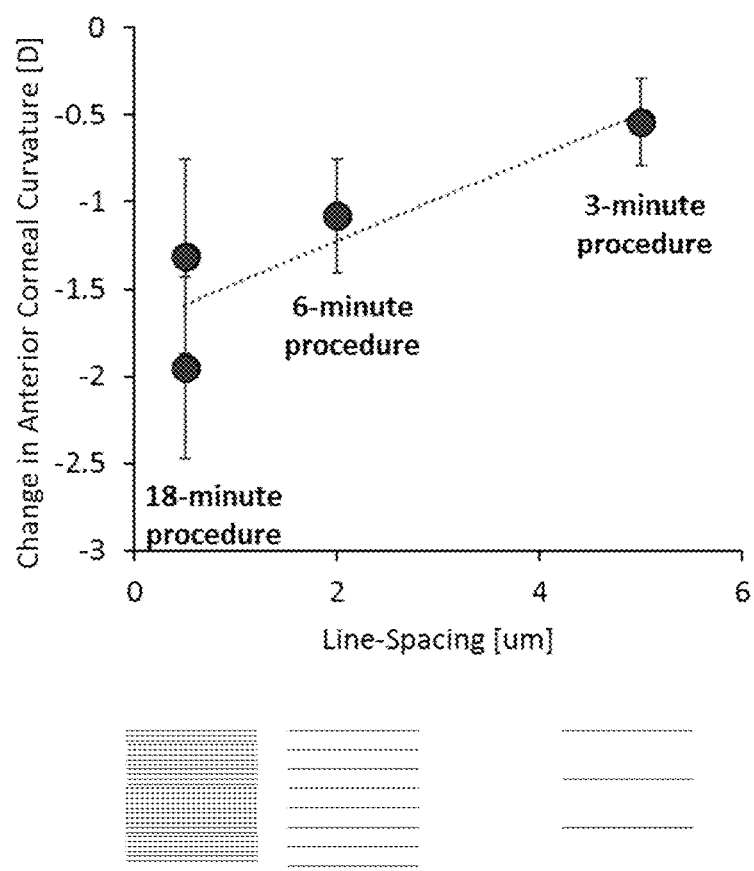
Figure 12. Effect of treatment duration, controlled by line-spacing in ex-vivo rabbit eyes.

VISION CORRECTION WITH LASER REFRACTIVE INDEX CHANGES

FIELD OF THE INVENTION

The present disclosure is directed to vision correction and more particularly to vision correction by modifying the index of refraction of optical polymeric lens material or of ocular tissue in the eye by a high-repetition, low-pulse energy femtosecond laser.

BACKGROUND

U.S. Publication No. 2008/0001320, the disclosure of which is incorporated herein by reference in its entirety, describes methods for modifying the refractive index of optical polymeric materials, such as intraocular lenses, corneal inlays, or contact lenses, using very short pulses from a visible or near-IR laser having a pulse energy from 0.5 nJ to 1000 nJ, where the intensity of light is sufficient to change the refractive index of the material within the focal volume, whereas portions just outside the focal volume are minimally affected by the laser light. Irradiation within the focal volume results in refractive optical structures characterized by a positive change in refractive index of 0.005 or more relative to the index of refraction of the bulk (non-irradiated) polymeric material. Under certain irradiation conditions and in certain optical materials, a change in refractive index of 0.06 was measured. In general, there are two types of intraocular lenses, referred to as pseudo-phakic IOLs and phakic IOLs. The former type replaces the eye's natural, crystalline lens, usually to replace a cataractous lens that has been removed. The latter type is used to supplement an existing lens and functions as a permanent corrective lens, which is implanted in the anterior or posterior chamber to correct refractive errors of the eye. The change in refractive index can be used to form patterned desired refractive structures in the optical polymeric material.

As opposed to modifying the refractive index in ophthalmic lenses such as intraocular lenses or contact lenses, U.S. Pat. No. 8,512,320, the disclosure of which is incorporated herein by reference in its entirety, discloses a method for correcting vision in a patient by modifying the refractive index of ocular tissue itself, such as cornea tissue or natural crystalline lens tissue. The method comprises identifying and measuring the degree of vision correction of the patient; and determining the position and type of refractive structures to be written into the cornea tissue of the patient to correct the patient's vision. The refractive structures are written by irradiating select regions of the cornea tissue with focused laser pulses having a wavelength in the visible or near-IR, e.g., from 400 nm to 900 nm, and a pulse energy from 0.01 nJ to 10 nJ. The refractive structures are characterized by a positive change in refractive index in relation to non-irradiated cornea tissue of the patient. Such process may be referred to as Intra-tissue Refractive Index Shaping (IRIS) in biological tissues or Intra-Polymer Refractive Index Shaping (IRIS) in optical polymers, such as intraocular lenses, contact lenses or corneal inlays.

U.S. Publication No. 2012/0310340, the disclosure of which is incorporated herein by reference in its entirety, describes a method for providing changes in refractive power of an optical device made of an optical, polymeric material by forming at least one laser-modified, gradient index (GRIN) layer disposed between an anterior surface and a posterior surface of the device by scanning with light pulses from a visible or near-IR laser along regions of the optical, polymeric material. The at least one laser-modified GRIN layer comprises a plurality of adjacent refractive segments, and is further characterized by a variation in index of refraction of at least one of: (i) a portion of the adjacent refractive segments transverse to the direction scanned; and (ii) a portion of refractive segments along the direction scanned. U.S. Publication 2012/0310223, the disclosure of which is incorporated herein by reference in its entirety, discloses a method of modifying the refractive index in ocular tissues wherein a laser-modified gradient index (GRIN) layer is formed directly in at least one of the corneal stroma and the crystalline lens.

In such processes, the irradiated regions of the optical tissue or optical polymeric material can take the form of two- or three-dimensional, area or volume filled refractive structures. The refractive structures are formed by scanning the laser over a select region of the optical tissue or polymeric material resulting in refractive optical structures that can provide spherical, aspherical, toroidal, or cylindrical correction to the optical tissue or a polymeric lens. In fact, any optical structure can be formed to yield positive or negative power corrections. Moreover, the optical structures can be stacked vertically or written in separate planes in optical tissue or the polymeric material to act as a single lens element.

There is an ongoing need for new and improved techniques and materials, and refractive corrector vision components resulting therefrom, for improving human vision. Such components may include IOLs for use following cataract surgery, or may be in the form of corneal inlays or other implantable vision correction devices, or contact lenses. There are also advantages and benefits that would result from such techniques and components allowing in-situ modification of refractive properties (e.g., refractive index, dioptric power) of such components, as well as direct modification of ocular tissue to provide corrected vision. There is further a need for improved techniques and materials which are directed towards providing refractive structures in such materials in shape controlled patterns which cover the majority of the clinically relevant optical zone of the eye (e.g., of circular zones of conventional pupil diameters).

SUMMARY

The present disclosure is directed towards various methods and systems wherein laser induced refractive index changes by focused femtosecond laser pulses in optical polymeric materials or ocular tissues is performed to modify optical properties of the optical polymeric materials or ocular tissues to address various types of vision correction, wherein shape changes in the optical polymeric materials or ocular tissues induced by patterns written with the laser pulses are either employed or minimized in the design of the modified optical polymeric materials or ocular tissues.

Specific embodiments of the disclosure include those set forth in the appended claims, and further embodiments as described in the specification.

In the various embodiments of the disclosure, one or more of the following features may be employed alone or in combination: the focused, visible or near-IR laser has a pulse energy from 0.01 nJ to 10 nJ; a multiple-photon-absorbing chromophore may be applied to the optical polymeric materials or ocular tissue prior to modifying the refractive index of the optical polymeric materials or ocular tissue; the multiple-photon-absorbing chromophore comprises a two-photon-absorbing chromophore; the ocular tissue comprises tissue of a lens; the ocular tissue comprises tissue of a cornea; locations defined by the focus spot are selected to form a structure selected from the group consisting of Bragg gratings, arbitrary wavefronts, microlens arrays, zone plates, and Fresnel lenses; the laser pulses are emitted at a frequency between 1 MHz and 10 GHz; the laser pulse frequency is between 10 MHz and 500 MHz; the laser pulse frequency is between 1 MHz and 100 MHz; the pulse width is between 10 fs and 1000 fs; the pulse width is between 10 fs and 100 fs; the laser pulses have an average power between 1 mW and 20 W; the laser pulses have an average power between 1 mW and 1,000 mW; the laser pulses have an average power between 10 mW and 10,000 mW; the laser pulses have a pulse energy between 0.01 nJ and 10 nJ; the laser pulses have a pulse energy between 0.1 and 2 nJ; the size of the focus spot is between 0.5 micrometer and 2 micrometer; the focus spot is scanned at a scanning speed between 0.1 micrometer/s and 10,000 mm/s; the focus spot is scanned at a scanning speed of at least 1 mm/s; the focus spot is scanned at a scanning speed of at least 10 mm/s; the focus spot is scanned at a scanning speed of at least 100 mm/s; the laser pulses have a wavelength between 350 and 1,300 nm; the laser pulses have a wavelength between 600 and 1,000 nm; the wavelength is between 700 and 900 nm; the laser pulses have a wavelength between 1,000 and 1,300 nm; the laser pulses have a wavelength between 350 and 600 nm.

BRIEF DESCRIPTION OF THE DRAWINGS

FIG. 4 illustrate conventional (left) and saturated (right) Fresnel lenses laser writing patterns shown in cross-section with equal height of 300 mW.

FIG. 5 illustrates OCT images of the same cat cornea before and after treatment.

FIG. 6. Change in anterior corneal curvature [diopters] for 6 cat eyes before and after laser treatment measured with optical coherence tomography (OCT).

FIG. 7. Change in ocular aberrations for 7 cat eyes before and after laser treatment, measured over a 4.5 mm diameter optical zone with a Shack-Hartmann wavefront sensor.

FIG. 8. Change in ocular power over time after the laser treatment in one cat eye (#7).

FIG. 9. Results of ex-vivo rabbit eye experiments for Rabbit Eyes 5 (left), 6 (center) and 8 (right).

FIG. 10. Apparatus for controlling and monitoring ocular pressure of ex-vivo rabbit eyes.

FIG. 11. Corneal topography rings images and power maps showing a central flattening of an ex-vivo rabbit cornea following fs-laser treatment.

FIG. 12. Effect of treatment duration, controlled by line-spacing in ex-vivo rabbit eyes.

DETAILED DESCRIPTION

Figure 1A:
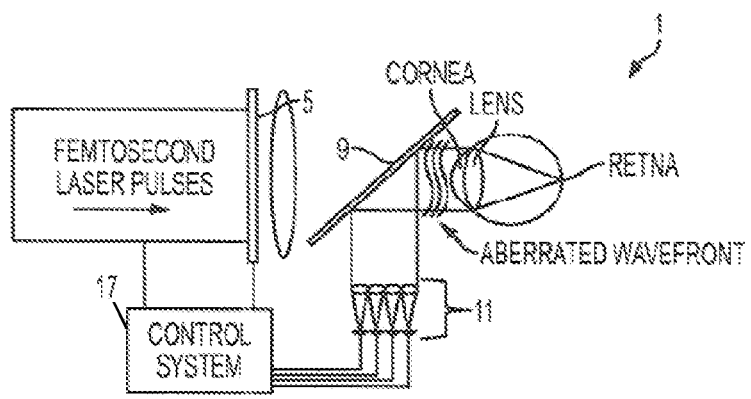
FIGS. 1A-1C show a device on which embodiments can be implemented.

As a material dependent phenomenon, femtosecond laser operating parameters associated with writing refractive index changes in optical materials can produce shape changes in the materials relative to their shape prior to writing of the refractive index changes. In optical polymer materials, particularly such materials with high water content, such writing can produce material expansions or contractions. In polymer materials, the writing may break polymer chains and/or bonds, e.g., opening up the polymer matrix and/or releasing monomer segments for dispersion elsewhere in the optical polymer materials, while dynamically replacing the monomers with water causing material expansion. Alternatively, the writing may tighten or cross-link polymer chains and/or bonds, e.g., squeezing the polymer matrix. In ocular tissues, particularly corneal tissue, such writing can produce material contractions or expansions. In living tissue, e.g., the writing may be a form of cross-linking of tissue such as collagen fibrils found in the corneal stoma layer allowing for material contraction, potentially enhanced with the influence of external pressures. The material expansions or contractions are most pronounced when writing close to the surfaces of the optical materials.

Dynamic effects of the writing in the optical materials can produce gradual changes in shape over time. The gradual shape changes can be exploited for controlling obsolescence to encourage lens replacements, for example, on a safe schedule. The dynamic effects can also be exploited to make gradual prescription changes toward a target prescription or to accommodate anticipated prescription changes.

Internal stresses can also influence the changes in shape accompanying the material expansions or contractions. For example, stresses associated with mounting the optical materials in a distorted state can influence shape changes associated with the material expansions or contractions. Unless the shape changes associated with internal stresses are otherwise managed or exploited, patterns are preferably written into the optical materials while the optical material is mounted in a low stress or more natural state.

For example, one way of writing both refractive index and associated shape changes in optical materials having an overall spherical shape is to write Fresnel or other diffraction patterns through minimally stressed spherical surfaces as a stepped or continuous spherical spiral.

The shape changes can be used to influence the optical properties of the materials as well as other functionalities such as conventional ballast for orienting the optical materials in wearers' eyes.

Operating parameters associated with the writing operations can be controlled to optimize either refractive index or shape changes, or both either separately or together. Refractive index changes and shape changes can be additive to each other in terms of optical power or optical effect, or they can be subtractive (i.e. having opposite signs). Refractive index changes and shape changes can also serve to produce different optical effects, such as, for example, the shape change could effect the spherical correction, and the refractive index change could be structured, typically in a separate layer, to effect an astigmatism correction or a higher order aberration correction or a multifocal (e.g., diffractive pattern). Generally, changes in refractive index can be more localized whereas changes in shape take place on a larger scale. Refractive index and shape changes can be effected together in different proportions by controlling writing parameters, including controlling focusing parameters such as numerical aperture to achieve differing spot sizes (e.g., cross-sections and depths).

In various embodiments, ametropia to be corrected may include, for example, myopia, hyperopia, astigmatism or presbyopia. In particular embodiments, the present disclosure relates to correcting higher-order errors of refracting power, and in particular, fourth-order errors of refracting power (spherical aberrations). Additional aberrations may also be corrected, including astigmatism, coma, trefoil, and any combination of these, as well as defocus and spherical aberrations. Further, custom correction for an individual's particular combination of aberrations and defocus may be corrected in a custom correction registered to their particular vision issues as diagnosed via wavefront abberometry, manifest refraction, topography, etc. Chromatic aberration can also be corrected using certain embodiments, for example a positive Diopter monofocal or multifocal diffractive add power may be used to counteract chromatic aberrations caused by the eye (either cornea or natural lens), contact lenses, intraocular lenses and/or corneal inlays, either individually or in combination (see for example, U.S. Pat. No. 6,830,332, which is incorporated by reference herein in its entirety for chromatic aberration corrections).

Laser induced refractive index change (LIRIC) description

Choosing the right laser parameters is critical for achieving IRIS in biological tissues. Not only does the femtosecond laser fluence at the objective focus have to be below the optical breakdown threshold of the tissue, it also had to be strong enough to induce some nonlinear changes, and the scan speed must be set within a specified range. In the past two decades, extensive experimental and theoretical work has been done to characterize laser-induced optical breakdown thresholds in different materials, including the cornea (Docchio, Sacchi & Marshall, 1986, Du, Liu, Korn, Squier & Mourou, 1994, Giguere et al., 2007, Loesel et al., 1996, Stern, Schoenlein, Puliafito, Dobi, Birngruber & Fujimoto, 1989, Stuart, Feit, Rubenchik, Shore & Perry, 1995, Tien, Backus, Kapteyn, Murnane & Mourou, 1999, Vogel et al., 2005) and the lens (Brazitikos, D'Amico, Bochow, Hmelar, Marcellino & Stangos, 1998, Li & Borkman, 1990, Vogel, Capon, Asiyo-Vogel & Birngruber, 1994). However, most of this work centered on the use of continuous wave (CW) lasers or on single pulses from low-repetition-rate lasers in which thermal diffusion time is much shorter than the time interval between adjacent pulses. Thus, each pulse is responsible for a change in the material. Indeed, it has been established that for pulses longer than 10 ps, the optical breakdown threshold fluence scales as the square root of the pulse duration (Du et al., 1994). For pulses shorter than 10 ps but longer than about 100 fs (which is the case with IRIS settings), the experimental results show a departure from this dependence. However, whether threshold fluence increases or decreases as pulse durations get shorter remains a challenging question (Stern et al., 1989, Stuart et al., 1995, Tien et al., 1999).

When high-repetition-rate femtosecond laser pulses are used, cumulative, free-electron-mediated chemical effects, photochemical bond breaking and thermal effects contribute to the laser-tissue interaction. As a result, the breakdown threshold fluence may be quite different from that predicted by current models (Vogel et al., 2005). Several studies on the effects of high-repetition-rate femtosecond lasers on fused silica and borosilicate glass have found that laser pulses greatly increased the temperature of the materials at the laser focus (Eaton, Zhang, Herman, Yoshino, Shah, Bovatsek & Arai, 2005a). Vogel calculated the temperature change in water would be >10° K with a 0.6 NA focusing lens and 100 fs laser pulses (Vogel et al., 2005), assuming that with each pulse, an energy density of 1 J/cm$^3$ at the center of the initial temperature distribution is deposited. Using very high-repetition-rate (93 MHz), ultra-short laser pulses (27 fs), it was found that the optical breakdown threshold for the 0.70 NA focusing condition in lightly-fixed corneal stroma and lens cortex to be 55 mW and 75 mW average laser power respectively (Ding et al., 2008). This corresponds to 0.6 nJ and 0.8 nJ pulse energies respectively, both lower than the optical breakdown power reported by König and colleagues using 1 nJ pulse energy, 170 fs pulse duration and 1.30 NA focusing in porcine corneas (König et al., 2002). By using 30 mW and 45 mW average laser power (0.3 nJ and 0.5 nJ pulses), it was able to induce IRIS, without accompanying photo-disruption and tissue destruction.

Experiments demonstrated that it is possible to cause low-scattering-loss, refractive index modifications in lightly-fixed cat cornea and lens using 93 MHz repetition rate, 27 fs laser pulses with 0.3 nJ and 0.5 nJ pulse energies. These modifications were visible only using DIC microscopy and were not associated with apparent tissue damage. They represent refractive index changes between 0.005±0.001 and 0.021±0.001. Preservation of IRIS over a month of refrigerated storage suggested that the femtosecond laser-induced modifications were likely to involve relatively long-term molecular/structural alterations. In related experiments involving silicone hydrogels, the micromachined gratings (and associated Raman spectra) were observed to persist for up to one year, even after drying and rehydration of the hydrogel (Ding, Cancado, Novotny, Knox, Anderson, Jani, Blackwell, Künzler & Smith).

Even relatively small refractive index changes induced in cornea and lens tissue can have a significant impact on optical power. Based on published values for the power (39D) and native refractive index (1.376) of the cat cornea (Hughes, 1977), IRIS should generate a change in corneal power ranging between 0.14 D and 0.56 D (assuming an index change between 0.005 and 0.02). Similarly, for the cat lens (power=53 D, refractive index of the homogeneous lens=1.554) (Hughes, 1977), the refractive index changes induced by micromachining should theoretically alter lenticular power by between 0.5 D and 0.7 D. The ultimate change in power is based on both the change in refractive index and the optical path length over which the refractive index is changed. In other words, the total refractive change is the change in refractive index multiplied times the length of the changed portion of the material. As such, even small changes over a longer path length can have significant refractive power, or a large refractive index change over a small path length could have a significant refractive power.

Improvement in refractive index change and/or writing speeds may be achieved by employing a laser wavelength in a range for which the ocular tissue is more inherently sensitive to 2-photon absorption. US 20110071509, the disclosure of which is incorporated herein by reference in its entirety, e.g., discloses more particularly a method for forming a refractive structure in a living eye, where the method includes the steps of directing and focusing a plurality of femtosecond laser pulses in a spectral region between about 350 nanometers (nm) to about 600 nm, and more particularly blue light, within a cornea or a lens of the living eye; controlling the intensity of the laser pulses to have an intensity sufficient to change the refractive index of the cornea or lens within a defined focal region, but below a damage threshold the cornea or lens, or at a level that will not photo-disrupt cornea or lens tissue outside of the focal region; and forming a refractive structure in the focal region of the cornea or the lens by scanning the laser pulses through a volume of the cornea or the lens. Each refractive structure is characterized by a change in refractive index, and exhibits little or no scattering loss.

Additionally or alternatively, a photosensitizer may be employed to chemically enhance the two-photon absorption properties of both tissues. Such photosensitization can result in an increase in (for example, at least a doubling of) the refractive index changes and an increase in laser writing speed (for example, greater than a 10× increase or even a several hundred fold increase in the micromachining speeds attained). The use of a photosensitizer is more specifically disclosed in U.S. Pat. No. 9,545,340, the disclosure of which is incorporated by reference herein in its entirety. Some multiphoton or two-photon absorbers may include fluorescein, coumarin, acetaminophen or riboflavin.

Ongoing experiments have generated information about the cellular and molecular mechanisms underlying IRIS in the living cornea, allowing us to gain critical knowledge that can be used to further manipulate the size, placement and design of micromachined patterns, as well as the magnitude of the refractive index changes with which they are associated. The ability to alter the native refractive index of the cornea and lens without causing significant tissue damage has important theoretical and practical implications. By understanding how laser power can be used to alter tissues non-destructively, and by understanding the nature of these alterations, we could open up an entirely new branch in the field of laser biology. Among other things, this could completely change our approach to laser refractive surgery, and to vision correction more generally. For instance, the preservation of tissue clarity during the treatment allows the application of IRIS for the creation of corneal fiducial markings that could be used to align eye trackers during LASIK, and for refractive corrections in a closed-loop approach, e.g. with specific benefit for the correction of higher-order aberrations, as well as for "touch-up corrections" of ocular surface defects. More broadly, the feasibility of IRIS in living tissues offers new possibilities for non-invasive alterations, marking or pattern-inscription within living organisms. From a theoretical stand-point, it also provides a unique opportunity to better understand and define the extent to which we can optically manipulate even large areas of living tissues without inducing a significant wound healing reaction.

Various ranges of parameters are particularly useful in implementing IRIS in the present disclosure. In treatment of the eye, the laser wavelength should be such that the tissues through which laser pulses pass are transparent to the pulses—for example, 350 nm-1600 nm, or more preferably 400 nm-1100 nm. There should also be limited or no damage to the retina; any significant change should be confined to the tissue located at the spot of focus of the pulses.

A laser pulse frequency (repetition rate) of 80-93 MHz is useful for many applications, as is a repetition rate of between 1 MHz and 100 MHz. A preferable range is from 1 MHz to 10 GHz, and more preferably from 10 to 500 MHz.

Linked to the pulse frequency is the average power. A preferable range is from 1 to 1,000 mW, and more preferably 10 to 100 mW, and more preferably still from 50 to 60 mW. The energy of each pulse should preferably be less than 1 nJ and more preferably less than 0.5 nJ, although a range from 0.01 to 10 nJ and more preferably from 0.1 to 2 nJ can be used.

A laser pulse width of 30 fs is useful for many applications. A preferable range is from 5 fs to 1 ps, including, e.g., greater than or equal to 20 fs, greater than or equal to 50 fs, greater than or equal to 100 fs, more preferably from 10 to 300 fs, and more preferably from 30 to 200 fs.

The scanning speed of the laser is preferably at least 0.4 μm/s, more preferably at least 0.1 mm/s, or at least 1 mm/s or at least 10 mm/s, and more preferably greater than 50 mm/s and higher. For example, scan speeds of 100 mm/s, 200 mm/s, 400 mm/s, 700 mm/s and up to 1,000 mm/s and even higher and all speeds in between are valuable and many have been demonstrated and are effective to reduce the treatment time. Apparatus which may be employed in the present disclosure and which is capable of obtaining such high scanning speeds is described, e.g., in WO 2015/006274, the disclosure of which is incorporated by reference herein in its entirety.

The wavelength should be one to which the tissues through which the laser pulses must pass are transparent. It should also preferably be just barely within the visible range for the patient (e.g., around 400 nm, or from 375 nm to 425 nm), within the visible range (e.g., 400 nm-750 nm), or outside of the visible range (e.g., near-infrared), so as not to bother the patient. In the near-infrared range, a wavelength of 780-810 nm is useful, as is a wavelength of 800 nm, as well as 1000-1040 nm. Further preferable ranges include 600-1,000 nm (and more preferably 700-900 nm) and above 1,000 nm (e.g., 1000-1300 nm).

The laser pulses are focused to a cross-sectional spot size that is preferably 1 μm. Preferable ranges include 0.5 μm to 2, 10, or 50 μm. Further the spot length along the z-axis (i.e. length or depth along the axis of the laser beam) may be of similar dimensions or different to those for the cross-sectional spot size. For example, the spot length along the z-axis may be in the range of 1-50 microns, or preferably from 1-20 microns or from 10-20 microns.

Various structures can be produced in the ocular tissue as well as polymers for optical lenses, such as contacts, intraocular lenses and corneal inlays. Examples include high refractive index structures such as Bragg gratings, microlens arrays, optical zone plates, diffraction patterns and Fresnel lenses, as well as a variety of refractive lenses and refractive multifocals. Further examples may include various extended depth of focus patterns, trifocal diffractive patterns, chromatic aberration corrections or higher order aberration corrections, such as spherical aberration or coma or astigmatism, including mixed astigmatism.

Preliminary experiments (Ding, Huxlin & Knox, 2007, Ding et al., 2008, Huxlin, Ding & Knox, 2008) showed that it is possible to change the refractive index of the lightly-fixed, mammalian cornea and lens without tissue destruction, a phenomenon termed Intra-tissue Refractive Index Shaping (IRIS). To achieve this, first measured, then reduced femtosecond laser pulse energies below the optical breakdown threshold of lightly-fixed post-mortem cat corneas and lenses. In both silicone and non-silicone-based hydrogels, this approach induced a significant change in refractive index without visible plasma luminescence or bubble formation (Ding et al., 2006).

Eight corneas and eight lenses were extracted under surgical anesthesia from five normal, adult domestic short-hair cats (*felis* cattus). To avoid decomposition and opacification prior to femtosecond laser micromachining, extracted feline tissues were immediately drop-fixed for 10 minutes (corneas) or one hour (lenses) in a solution consisting of 1% paraformaldehyde in 0.1M phosphate buffered saline (PBS), pH 7.4. Lenses were then cut into 500 µm thick slices using a HM650V vibratome (Microm International), after which lens sections and whole corneas (also ~500 µm thick) were immersed in a mixture of 30% ethylene glycol+ 30% sucrose in 0.1M PBS, pH7.4 at 4° C. Storage in this solution minimized tissue swelling and loss of transparency. Small pieces of tissue, ~1 cm² were then flattened onto a clear glass slide (1×3 inches, 1mm thick, Surgipath Medical Industries Inc., IL). In the case of corneal pieces, this was done with the epithelium facing up and the endothelium facing down. A glass coverslip (Corning No. 0211 Zinc Titania glass) was placed on the top of each piece, stabilizing it for the duration of the experiment. The ethylene glycol/ sucrose storage solution was used as mounting medium to minimize dehydration of the cornea and lens tissue samples since these effects are known to alter the refractive index and transparency of both these tissues (Fisher, Masiello, Goldstein & Hahn, 2003, Meek, Dennis & Khan, 2003, Patel, Alio & Perez-Santonj a, 2004).

Femtosecond laser micro-machining was conducted as previously described in hydrogels (Ding et al., 2006). The laser source was a Kerr-lens mode-locked Ti:Sapphire laser (K-M Labs). The laser oscillator generated pulses averaging 300 mW, 27 fs in duration, with a 93 MHz repetition rate at 800 nm wavelength. A continuously variable, metallic, neutral density filter inserted into the optical path, was used to adjust the incident laser power onto each cat cornea and lens piece. Pulses were focused 100 µm below the tissue surface using a 60×, 0.70 NA Olympus LUCPlanFLN microscope objective with an adjustable working distance of 1.5-2.2 mm. Because the large amount of glass within the microscope objective induced significant chromatic dispersion into the femtosecond laser pulses, broadening the pulse durations, a standard extra-cavity-prism double-pass configuration was used to compensate for the dispersion and maintain the ultra-short pulse duration. By carefully adjusting this dispersion compensator, nearly transform-limited 27 fs duration pulses were obtained at the focal point of the focusing objective, as measured by a collinear auto-correlator using 3rd order surface harmonic generation (Meschulach, Barad & Silberberg, 2003, Squier, Fittinghoff, Barty, Wilson, Muller & Brakenhoff, 1998). During IRIS, the slide containing the biological tissue samples was mounted on a 3D scanning platform consisting of a Physik Instrumente P-622.2CD XY scanning stage with 250 µm travel range and 0.7 nm close-loop resolution, and a Newport VP-25XA linear servo Z-axis scanning stage with 25 mm travel range and 100 nm resolution. An infrared CCD camera was used to monitor the micromachining process and the generation of visible plasma luminescence in real-time.

A first step was to establish thresholds for the optical breakdown of lightly-fixed feline cornea and lens. The neutral density filter was first adjusted to minimize the focused incident laser power on the cornea and the lens below their breakdown thresholds (Giguere et al., 2007, Loesel et al., 1996). Adjusting the neutral density filter then progressively increased the incident laser power. The breakdown threshold power was reached when visible plasma luminescence suddenly appeared and strong scattering light as well as laser-induced damage became visible. With a 0.70 NA long-working-distance objective, the measured breakdown thresholds for cat cornea and lens were ~55 mW and 75 mW average laser power respectively, which corresponds to pulse energies of 0.6 nJ and 0.8 nJ.

Once tissue breakdown thresholds were established, the focused laser power was lowered gradually by carefully adjusting the neutral density filter until lines could be micromachined without the induction of bubbles or burns. Average laser power settings at which this could be done were 30 mW in the cornea and 45 mW in the lens, corresponding to pulse energies of about 0.3 nJ and 0.5 nJ respectively. These values lay between those used for imaging and measured breakdown thresholds. The gratings were micromachined in the horizontal plane within the stromal layer of each corneal piece and the cortex of each lens at a constant speed of 0.7 µm/s for the cornea and 1 µm/s for the lens. The spherical aberration at the laser focus induced by refractive index mismatch was compensated by adjusting the correction collar of the focusing microscope objective in order to achieve the smallest possible laser-affected region along the laser propagation direction (Ding et al., 2006).

Exposure of lightly-fixed cat corneal and lenticular tissue to 0.3 nJ or 0.5 nJ femtosecond laser pulses (28 mW or 47 mW average laser power) respectively resulted in the reliable creation of line gratings about 100 µm below the epithelial surface or 100 µm below the lens surface in all test samples. When imaged immediately after micromachining, individual grating lines could be clearly observed and distinguished with differential interference contrast (DIC) microscopy, but they were practically invisible when viewed under bright field (BF) transmission microscopy. This could be interpreted as the grating lines having very low scattering properties, which is in contrast to the destructive tissue changes observed with laser pulse energies above the optical breakdown threshold of the tissues. Using the knife-edge method (Smith, 2000), ascertained that the laser focus diameter was 2.5 µm in air, which was much bigger than the micromachined line-widths. Thus, it appears that only the central part of the laser focal area had sufficient intensity to modify corneal and lens tissues.

To assess whether the gratings generated in corneal and lens pieces were associated with a change in refractive index, the slides containing the tissue were first placed under an Olympus BX51 optical microscope where gratings were localized using DIC imaging. A low-power 632.8 nm He—Ne laser was then used to irradiate the gratings, generating a diffraction pattern that was captured by a digital camera and used to calculate the refractive index changes attained, as described previously (Ding et al., 2006).

In brief, a power meter measured the intensity of the $0^{th}$-$3^{rd}$ order diffracted light from the gratings and the different order diffraction efficiencies were obtained by calculating the ratios between the intensity of the $1^{st}$, $2^{nd}$ and $3^{rd}$ to the $0^{th}$ order diffraction light. Since the intensity distribution of the diffraction pattern of a phase grating is proportional to the square value of the Fourier Transform of the transmittance function of the grating (Born & Wolf, 1970), one particular value of refractive index change matches only one particular diffraction efficiency value (Ding et al., 2006). To reduce measurement error of the diffraction order intensities, five measurements were collected on each grating, calculating the average value obtained and its standard deviation. In principle, the spatial distribution of the refractive index change within the micromachined region was a small-scale gradient-index structure. The index profile was presumed to be uniform within the grating lines, which were only 3 µm deep because the spherical aberration at the focal point was corrected (Ding et al., 2006).

Because displacement of the stromal collagen lamellae as a result of post-mortem corneal swelling could not be completely avoided the scattering effect from the $0^{th}$ order diffraction light was very strong obscuring the $1^{st}$ order diffraction light (Meek et al., 2003). Thus, only the $2^{nd}$ and $3^{rd}$ order diffraction efficiencies of each grating could be measured and used to calculate an approximate refractive index change in corneal pieces. Because tissue swelling and opacification were minimal in slices of lens cortex, the $0^{th}$ through $3^{rd}$ order diffraction light could be measured clearly and $1^{st}$ and $2^{nd}$ order diffraction efficiencies were used to calculate the induced refractive index change. Although single diffraction efficiency is usually sufficient to calculate refractive index, $1^{st}/2^{nd}$ or $2^{nd}/3^{rd}$ combinations were measured to confirm that the index changes calculated were consistent through different diffraction orders, assuming that the refractive index of cat corneal stroma and lens cortex were 1.376 and 1.400 respectively (Hughes, 1977). For corneal stroma, the index changes induced by the laser in the multiple samples ranged between 0.005±0.001 and 0.01±0.001. For cat lens cortex, index changes were larger, ranging between 0.015±0.001 and 0.021±0.001.

After micromachining, each cornea and lens piece was stored in ethylene glycol/sucrose solution at 4° C. After one month, each piece was re-mounted onto a new glass slide for imaging and a repeat of the diffraction light intensity measurements. This allowed assessing whether the RI change initially observed had been maintained during storage. A first observation was that although the storage solution significantly slowed corneal swelling and opacification, it did not completely prevent either. In spite of this, DIC microscopy was able to reveal the grating structures initially micromachined.

For both corneal and lens slices, the diffraction light distribution of one-month old gratings was not significantly different than that obtained right after the gratings' creation. In the corneal pieces, the scattering light from the $0^{th}$ order diffraction still obscured the $1^{st}$ order diffraction. However, the $2^{nd}$, $3^{rd}$, and even $4^{th}$ order diffractions were visible and measurable. In the lens pieces, the $1^{st}$, $2^{nd}$ and $3^{rd}$ order diffraction were visible. The refractive index change after one month of storage still ranged between 0.005±0.001 and 0.01±0.001 for corneal pieces and between 0.015±0.001 and 0.021±0.001 for lens slices.

IRIS can be further potentiated by increasing two-photon absorption (TPA) or other multi-photon absorption of the cornea and lens. In early work with native hydrogels, femtosecond micromachining caused index changes in the range of +0.02 to +0.06, with very slow scanning speeds, as slow as 0.4 microns per second (Ding et al., 2006). The index changes attained in the cat cornea were small (~0.005-0.01) and background scattering made the features difficult to detect. Larger index changes were written in 500 µm thick slices of cat lens (~0.015-0.021), but all at very low scanning speeds (0.7 to 1 µm/s).

A reason why writing speeds were so slow in the cornea and the lens in early tests is that these clear biological tissues possess natively low two-photon absorption (TPA) properties. Thus, it was hypothesized that if the TPA of cornea and lens could be increased through the incorporation of a two-photon absorbing chromophore, this should theoretically increase the rate and magnitude of IRIS in these tissues. Sodium Fluorescein is one such chromophore, which is already commonly used in ophthalmic (and medical) practice. It is non-toxic to the living eye and can even be injected intravenously (e.g. for retinal angiography). To test the hypothesis, lightly-fixed cornea and lens pieces were incubated in a 25% solution of Sodium Fluorescein in ethylene glycol/sucrose/PBS overnight. Both tissue types readily absorbed the chromophore and turned slightly orange. They were then rinsed and IRIS was performed as described above. In Fluorescein-treated cat corneas, scanning speeds of 1 mm/s (~1,400× faster than in non-treated corneas) were attained and used to create multiple lines that were several mm long, and whose refractive index change averaged 0.02 (up to 4× larger than in non-treated corneas). Just as in the non-fluorescein treated corneas, these features were long-lived, lasting through several months of refrigerated storage.

Femtosecond laser treatment is performed under surgical or topical anesthesia as previously described for conventional laser refractive surgery (Bühren, Yoon, Kenner, MacRae & Huxlin, 2007b, Nagy et al., 2007). The subjects are placed into a specially designed head-mount, which will hold them in a supine position, with the eyes facing directly upwards. A drop of 0.5% Proparacaine Hydrochloride (or other ophthalmic anesthetic agent) will be placed in the eye to be treated. One to two drops of 20% NaFluorescein in a 10% solution of dimethyl sulfoxide (DMSO) in Celluvisc will also be administered to each eye to be treated in order to increase the two-photon absorption rate of the cornea. Pilot experiments show that 10 minutes is sufficient to allow penetration of the fluorescein chromophore through the entire thickness of the cornea. Lower and higher concentrations of Na Fluorescein also work, but the amount of time required for penetration increases at lower concentrations. The corneal surface can then be kept moist with the application of saline or ophthalmic moistening agents. Once corneal reflexes have disappeared, the subject can then undergo IRIS treatment over a circular (or otherwise shaped) area 6 mm (or other dimensions, as required) in diameter, in the center (or other location) of its cornea, at a depth of 100 µm (or other depths) below or within the surface epithelium. Other positional parameters can be used if needed. The eye can be kept immobile during the laser treatment by a fixation target or by conjunctival structures, which will be removed at the end of the operation. An infrared CCD camera is used to monitor the micromachining process and the generation of visible plasma luminescence in real-time. The treatment should take about 5-10 minutes per eye, after which the subject will be recovered as clinically prescribed.

A similar protocol, with the major difference being that the Na Fluorescein solution might have to be injected into the anterior chamber of the eye, could be used to enhance TPA in the living lens. IRIS could be performed in the lens by simply using a longer-working-distance focusing objective to focus the femtosecond laser beam into the lens in situ.

In order to assess whether chemical fixation of the cornea with paraformaldehyde was critical to attaining IRIS in the cornea, IRIS on a non-fixed (fresh), post-mortem cat cornea immediately after enucleation was performed. Several small gratings were inscribed one above the other in the corneal stroma and they were imaging with optical coherence tomography (OCT). Stacking several gratings together assured that the OCT, with a resolution of ~10 µm, could actually resolve these features, given that individual IRIS lines were only 1-3 µm thick. The results of this experiment was reported at an ARVO meeting (Huxlin et al., 2008). Thus, while fixation may influence the magnitude of RI change attained, IRIS does not actually require it.

IRIS does not change the Raman spectrum of hydrogels— changes in refractive index, not material composition or chemistry. Balafilcon A hydrogel polymer (Bausch & Lomb, USA) was used for this experiment, whose goal was to gain insight into the mechanisms by which femtosecond micromachining achieved its refractive index change in hydrated, optically clear but non-biological materials. The chemical components of the hydrogel used (Balafilcon A) included tris-(trimethylsiloxy)-silyl propylvinyl carbamate (TPVC), N-vinyl pyrrolidone (NVP) and other types of silicones (Karlgard, Sarkar, Jones, Moresoli & Leung, 2004). Balafilcon A contains 36% water by weight and has an average refractive index of 1.4220 (Ding et al., 2006). The cutoff wavelength of its transmission spectra are within the range of 300 to 350 nm, and its transmissivity at 800 nm is ~83% (Ding et al., 2006). A Kerr-lens mode-locked Ti:Sapphire femtosecond laser oscillator (K-M Labs), generating pulses of 300 mW average power, 27 fs pulsewidth and 93 MHz repetition rate at 800 nm was focused into the hydrogels using a 60×0.70 NA Olympus LUCPlanFLN long-working-distance objective. Throughout the whole experimental process, the hydrogel samples were mounted in a Borate Buffered Saline (BBS) solution between two cover glass slides and maintained their water-content. A 3D scanning platform formed by three Newport VP-25XA linear servo stages with 100 nm resolution was employed to move the hydrogel samples transversely to the direction of the laser beam. Smooth lines 40 μm long were inscribed just below the hydrogel surface using 1.3 nJ pulse-energies, which were below the optical breakdown threshold of the material. These low pulse-energies created a 0.06 refractive index change along the lines. Using the same knife edge method reported previously (Ding et al., 2006), a laser focal diameter of about 2.5 μm was measured. This focal diameter gave rise to laser-irradiated lines about 1 μm wide and 3 μm deep.

In order to check for structural modifications in the machined region, several Raman spectra were measured in 400 nm steps both within and next to the micromachined lines using a 3 mW, 632.8 nm HeNe laser. In both spectra, several Raman peaks were detected over the broad background fluorescence. Differences in the background fluorescence of the two spectra were first measured since some of the defects generated by MHz femtosecond laser pulses are known to increase fluorescence intensity in fused silica (Reichman, Krol, Shah, Yoshino, Arai, Eaton & Herman, 2006). Here however, no significant changes in background fluorescence were detected. The Raman signal was then calculated by subtracting the background fluorescence from the original spectrum. The Raman peaks could be assigned to different material bonds activities, but most importantly, the Raman spectra obtained from the machined region were almost identical to the Raman spectra obtained from the untreated regions of hydrogel, suggesting that the micromachining process did not induce significant structural and chemical changes in the hydrogel polymer.

Figure 1B:
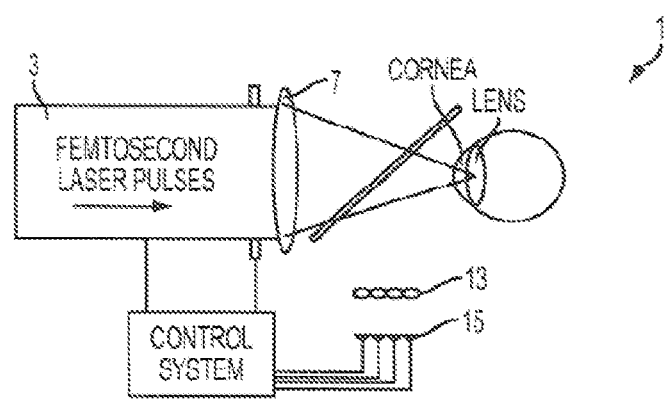
Figure 1C:
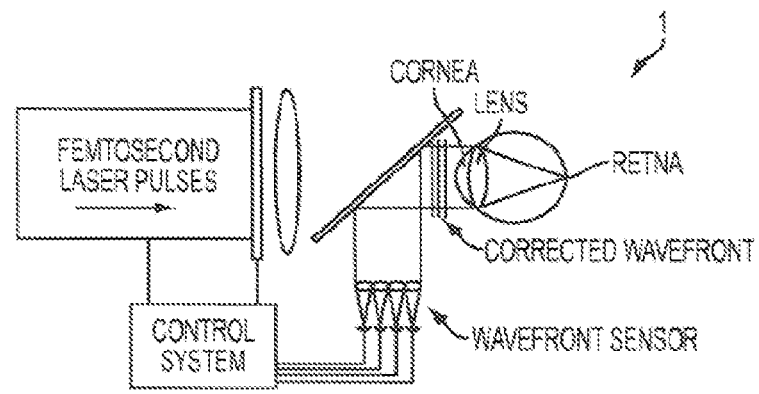

FIGS. 1A-1C show a schematic diagram of a device 1 which may used to carry out various embodiments of the disclosure. The device 1 includes a laser 3 for emitting femtosecond laser pulses, a shutter 5, a focusing lens 7, a dichroic mirror 9, a wavefront sensor 11 having a lenslet array 13 and a detector array 15, and a control system 17 for controlling the operations described herein.

As illustrated in FIGS. 1A-1C, the process would include the following steps: (1) using a wavefront sensor to detect and measure the lower and higher order aberrations along the optical path of a given eye, (2) calculating the topography and magnitude of refractive index changes required to achieve the necessary aberration correction, (3) focusing the femtosecond laser pulses either into the cornea or intraocular lens in order to carry out the micromachining necessary to induce the required refractive index change. Once the micromachining is complete, the wavefront sensor would be used once again to check the correction of the ocular wavefront. Since the resolution of the femtosecond laser micromachining is about 1 μm, this noninvasive method could be used as a complement or an alternative method for current customized wavefront correction methods.

In FIG. 1A, the shutter 5 is closed for detection of wavefront aberration from the optical path through the wavefront sensor 11, using aberrated light A reflected from the retina R of the eye E. In FIG. 1B, the shutter is open, and light pulses P from the femtosecond laser 3 are used to correct the aberration by locally changing the index in the cornea C or the lens L. In FIG. 1C, after femtosecond laser micromachining, the wavefront correction is verified once again using the wavefront sensor.

In particular embodiments, refractive corrector elements may be formed by irradiating an optical, polymeric material, or by direct writing into the human cornea, with very short laser pulses of light as described in U.S. Publication Nos. 2008/0001320, 2009/0287306, 2012/0310340 and 2012/0310223 incorporated by reference herein, where such short laser pulses are of sufficient energy such that the intensity of light within the focal volume will cause a nonlinear absorption of photons (typically multi-photon absorption) and lead to a change in the refractive index of the material within the focal volume, while the material just outside of the focal volume will be minimally affected by the laser light. The femtosecond laser pulse sequence pertaining to an illustrative embodiment, e.g., operates at a high repetition-rate, e.g., 10 MHz, 50 MHz, 80 MHz or higher, and consequently the thermal diffusion time (>0.1 μs) is much longer than the time interval between adjacent laser pulses (~11 ns). Under such conditions, absorbed laser energy can accumulate within the focal volume and increase the local temperature. This thermal mechanism likely plays a role in the formation of laser-induced refractive structures in optical, polymeric materials. Moreover, the presence of water in the polymeric material is believed to advantageously influence the formation of the refractive structures. As such, optical hydrogel polymers provide greater processing flexibility in the formation of the refractive structures as compared to zero or low water content optical polymers, e.g., the hydrophobic acrylates or low-water (1% to 5% water content) acrylate materials. The irradiated regions exhibit little or no scattering loss, which means that the resulting refractive structures that form in the focal volume are not clearly visible under appropriate magnification without phase contrast enhancement. In other words, the refractive structures are virtually transparent to the human eye without some form of image enhancement. The change in refractive index in the irradiated regions may be either positive or negative, depending on the combination of materials and wavelengths used. An optical material is a polymeric material that permits the transmissions of at least 80% of visible light through the material, that is, an optical material does not appreciably scatter or block visible light.

According to specific embodiments, refractive correctors may be formed by providing an optical, polymeric lens material having an anterior surface and posterior surface and an optical axis intersecting the surfaces; and forming at least one laser-modified layer disposed between the anterior surface and the posterior surface with light pulses from a laser by scanning the light pulses along regions of the optical, polymeric material to cause changes in the refractive index of the polymeric lens material. In such embodiment, the at least one laser-modified layer forms at least part of a desired refractive element formed to compensate for at least one vision problem as further described herein.

According to further embodiments, a refractive property of ocular tissue in an eye is modified by forming at least one optically-modified layer in at least one of the corneal stroma and the crystalline lens ocular tissue in an eye by scanning light pulses from a laser focused in the corneal stroma or crystalline lens ocular tissue along regions of the corneal stroma or crystalline lens ocular tissue to cause changes in the refractive index within the ocular tissue to form a modified corneal stroma or crystalline lens. In such embodiment, the at least one optically-modified layer forms at least part of a desired refractive element formed to compensate for at least one vision problem as further described herein.

Femtosecond laser pulse writing methods may be more advantageously carried out if an optical polymeric material, such as, e.g., an optical hydrogel material, includes a photosensitizer, as more particularly taught in U.S. Publication Nos. 2009/0287306 and 2012/0310340 incorporated by reference herein. The presence of the photosensitizer permits one to set a scan rate to a value that is at least fifty times greater, or at least 100 times greater, than a scan rate without a photosensitizer present in the material, and yet provide similar refractive structures in terms of the observed change in refractive index of the material in the focal volume. Alternatively, the photosensitizer in the polymeric material permits one to set an average laser power to a value that is at least two times less, more particularly up to four times less, than an average laser power without a photosensitizer in the material, yet provide similar refractive structures. A photosensitizer having a chromophore with a relatively large multi-photon absorption cross section is believed to capture the light radiation (photons) with greater efficiency and then transfer that energy to the optical polymeric material within the focal volume. The transferred energy leads to the formation of the refractive structures and the observed change in the refractive index of the material in the focal volume. Some examples of such photosensitizers include sodium fluoroscein, coumarin, riboflavin or various UV-blockers, such as UVAM or methine dyes.

A 60×0.70 NA Olympus LUCPlanFLN long-working-distance microscope objective with variable spherical aberration compensation may be employed to laser-write refractive segments. As indicated by the following equation $$\Delta T(r, z, t=0) = \frac{\beta \tau_P [I(0,0)]^2 \exp\left[-4\left(\frac{r^2}{a^2} + \frac{z^2}{b^2}\right)\right]}{c_p \rho}$$

the localized instantaneous temperature depends on both the pulse intensity and the magnitude of the two-photon absorption (TPA) coefficient. In order to produce an optical modification of a material that is of purely refractive character, i.e., non-absorbing or scattering, it is important to avoid optical damage, i.e., observed burning (scorching) or carbonization of the polymeric material. Such material or optical damage can be caused by excitation intensities exceeding a critical free-electron density. For hydrogel polymers containing a fair amount of water, the optical breakdown threshold is much lower than that in silica glasses. This breakdown threshold limits the pulse energy (in many cases to approximately 0.1 nJ to 20 nJ) that the hydrogel polymers can tolerate, and yet provide the observed changes in the refractive index within the focal volume.

Another way to increase energy absorption at a given intensity level is to increase the nonlinear absorption coefficient β by doping the optical, polymeric material with a particular chromophore and tuning the short pulse laser near a two-photon transition of the chromophore. In this regard, optical, hydrogel materials doped with a non-polymerizable photosensitizer or a polymerizable photosensitizer have been prepared. The photosensitizer may include a chromophore having a two-photon, absorption cross-section of at least 10 GM between a laser wavelength range of 750 nm to 1100 nm. In the former case of a non-polymerizable photosensitizer, solutions containing a photosensitizer may be prepared and the optical, hydrogel polymeric materials may be allowed to come in contact with such solutions to allow up-take of the photosensitizer into the polymeric matrix of the polymer. In the later case of a polymerizable photosensitizer, monomers containing a chromophore, e.g., a fluorescein-based monomer, may be used in the monomer mixture used to form the optical, polymeric material such that the chromophore becomes part of the polymeric matrix. Further, one could easily use a solution containing a non-polymerizable photosensitizer to dope an optical, polymeric material that had been prepared with a polymerizable photosensitizer. Also, it is to be understood that the chromophoric entities could be the same or different in each respective photosensitizer.

The concentration of a polymerizable, monomeric photosensitizer having a two-photon, chromophore in an optical material, preferably an optical, hydrogel material, can be as low as 0.05 wt. % and as high as 10 wt. %. Exemplary concentration ranges of polymerizable monomer having a two-photon, chromophore in an optical, hydrogel material is from 0.1 wt. % to 6 wt. %, 0.1 wt. % to 4 wt. %, and 0.2 wt. % to 3 wt. %. In various aspects, the concentration range of polymerizable monomer photosensitizer having a two-photon, chromophore in an optical, hydrogel material is from 0.4 wt. % to 2.5 wt. %.

Due to the high repetition rate pulse sequence used in the irradiation process, the accumulated focal temperature increase can be much larger than the temperature increase induced by a single laser pulse. The accumulated temperature increases until the absorbed power and the dissipated power are in dynamic balance. For hydrogel polymers, thermal-induced additional crosslinking within the polymer network can produce a change in the refractive index as the local temperature exceeds a transition temperature. The refractive index change may be positive or negative. If the temperature increase exceeds a second threshold, a somewhat higher temperature than the transition temperature, the polymer is pyrolytically degraded and carbonized residue and water bubbles are observed. In other words, the material exhibits visible optical damage (scorching). Each of the following experimental parameters such as laser repetition rate, laser wavelength and pulse energy, TPA coefficient, and water concentration of the materials should be considered so that a desired change in the refractive index can be induced in the hydrogel polymers without optical damage.

The pulse energy and the average power of the laser, and the rate at which the irradiated regions are scanned, will in-part depend on the type of polymeric material that is being irradiated, how much of a change in refractive index is desired and the type of refractive structures one wants to create within the material. The selected pulse energy will also depend upon the scan rate and the average power of the laser at which the refractive structures are written into the polymer material. Typically, greater pulse energies will be needed for greater scan rates and lower laser power. For example, some materials will call for a pulse energy from 0.05 nJ to 100 nJ or from 0.2 nJ to 10 nJ.

Within the stated pulse energies above, the optical, hydrogel polymeric material may be irradiated at a scan rate of at least 0.1 mm/s, or at least 1 mm/s or at least 10 mm/s, and can range, e.g., up to 50 mm/s or even higher. For example, scan speeds of 100 mm/s, 200 mm/s, 400 mm/s and up to 700 mm/s and even higher and all speeds in between are valuable and many have been demonstrated and are effective to reduce the scan time. Apparatus which may be employed in the present disclosure and which is capable of obtaining such high scanning speeds is described, e.g., in WO 2015/006274, the disclosure of which is incorporated by reference herein in its entirety, and may include, for example, scan stages, spinning polygonal mirrors, galvo mirrors, circular stages, etc. and any combinations thereof.

Within the stated pulse energies and scan rates above, the average laser power used in the irradiation process may be, e.g., from 10 mW to 3 watts or more, or 10 mW to 800 mW, or from 40 mW to 400 mW.

In one example, the average pulse energy may be from 0.2 nJ to 10 nJ and the average laser power may be from 40 mW to 220 mW. The laser also may operate within a wavelength of 500 nm to 1200 nm, or 650 nm to 950 nm or in the 1030 to 1050 nm range. Within the stated laser operating powers, the optical, hydrogel polymeric material may be irradiated at a scan rate, e.g., of greater than 4 mm/s, and preferably at greater than 10 mm/s. In further examples using average laser powers greater than 200 mW, the scan rates may range above 10 mm/s, even as high as 500 mm/s or higher.

A photosensitizer will include a chromophore in which there is little or no intrinsic linear absorption in the spectral range of 600-1100 nm. The photosensitizer is present in the optical, hydrogel polymeric material to enhance the photo-efficiency of the two-photon absorption required for the formation of the described refractive structures. Photosensitizers of particular interest include, but are not limited to, the following compounds. The compounds below are merely exemplary. Additional examples may include UVAM, other UV dyes used in contacts or IOLs, methine dyes, riboflavin, acetaminophen, and so forth.

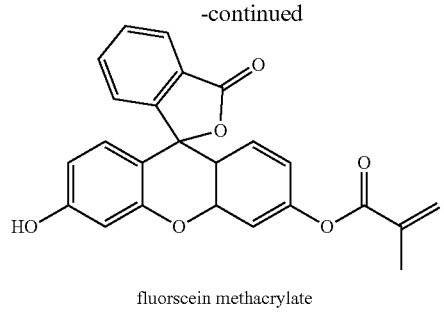

coumarin-1

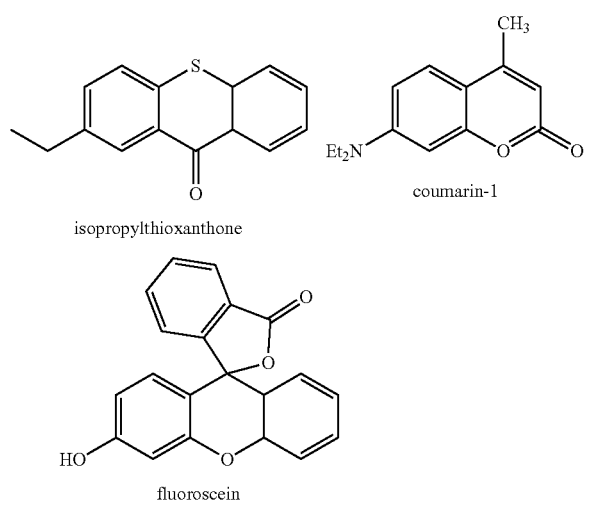

fluoroscein

-continued fluorscein methacrylate

As described in U.S. Publication Nos. 2009/0287306 and 2012/0310340 in greater detail in the Example sections, a commercial IOL material, Akreos®, presently marketed by Bausch & Lomb, was subjected to laser irradiation according to the processes described therein. An Akreos® IOL is a HEMA-based, hydrogel material with 26% to 28% water content. The micromachining process was used to imprint refractive structures in an Akreos® IOL without photosensitizer and an Akreos® IOL doped with a solution containing 17 wt. % coumarin-1. The irradiation experiments were conducted with both dry and hydrated materials. The refractive structures formed only in the hydrated materials. In brief, the magnitude of the measured change in refractive index was at least ten times greater in the Akreos® IOL doped with the coumarin solution at a given scan rate and an average laser power than the Akreos® IOL without the coumarin.

In another illustrative aspect described in U.S. Publication Nos. 2009/0287306 and 2012/0310340, a balafilcon A silicone hydrogel was prepared by adding fluorescein monomer (0.17% by weight) as a polymerizable photosensitizer to the polymer monomer mixture. The balafilcon A doped with fluorescein was then subjected to laser radiation according to the processes described therein. Again, the described irradiation process was used to imprint refractive structures in the silicone hydrogel without photosensitizer and the silicone hydrogel doped with 0.17 wt. % fluorescein monomer. Again, experiments were conducted with both dry and hydrated materials, and again, the refractive structures formed only in the hydrated materials. In brief, the magnitude of the measured change in refractive index was at least ten times greater in the balafilcon A silicone hydrogel doped with 0.17 wt. % fluorescein monomer at an average laser power of 60 mW than balafilcon A without the photosensitizer. This 10-fold difference in change in refractive index was observed even with a 10-fold increase in scan rate in the photosensitized material; i.e., 0.5 mm/s in the undoped material and 5.0 mm/s in the photosensitized material.

The laser may generate light with a wavelength in the range from violet to near-infrared. In various aspects, the wavelength of the laser may be in the range from 400 nm to 1500 nm, from 400 nm to 1200 nm, or from 650 nm to 950 nm.

In an exemplary aspect, the laser may be a pumped Ti:sapphire laser with an average power of 10 mW to 1000 mW or higher. Such a laser system will generate light with a wavelength of approximately 800 nm. In another exemplary aspect, an amplified fiber laser that can generate light with a wavelength from 1000 nm to 1600 nm may be used.

The laser may have a peak intensity at focus of greater than $10^{13}$ W/cm$^2$. At times, it may be advantageous to provide a laser with a peak intensity at focus of greater than $10^{14}$ W/cm$^2$, or greater than $10^{15}$ W/cm$^2$.

The ability to form refractive structures in optical polymeric materials provides an important opportunity to an ophthalmic surgeon or practitioner to modify the refractive index of an optical device, e.g., an intraocular lens or corneal inlay, following implantation of the device into an eye of a patient. The method allows the surgeon to correct aberrations as a result of the surgery. The method also allows the surgeon to adjust the refractive properties of the lens or inlay by adjusting the refractive index in the irradiated regions based on the vision correction required of each patient. For example, starting from a lens of selected power (will vary according to the ocular requirements of the patient), the surgeon can further adjust the refractive properties of the lens to correct a patient's vision based upon the individual needs of the patient. In essence, an intraocular lens would essentially function like a contact lens or glasses to individually correct for the refractive error of a patient's eye. Moreover, because the implanted lens can be adjusted by adjusting the refractive index of select regions of the lens, post-operative refractive errors resulting from pre-operative measurement errors, variable lens positioning during implantation, and wound healing (aberrations) can be corrected or fine tuned in-situ.

The irradiated portions of the optical, hydrogel polymeric material may exhibit a positive change in refractive index of about 0.01 or more. In one embodiment, the refractive index of the region will increase by about 0.03 or more. As disclosed in U.S. Publication Nos. 2009/0287306 and 2012/0310340, a positive change in refractive index in a hydrated, Akreos® IOL material of about 0.06 has been measured. In some cases the refractive index change will be negative (i.e. reducing the refractive index relative to the native material index before radiation). The magnitude of the negative change has been shown to be about 0.01 or greater (i.e. −0.01 to −0.06 or even more). As disclosed for example in Femtosecond Laser Writing of freeform gradient index microlenses in hydrogel-based contact lenses, Gandara-Montano et al., in Optical Materials Express, vol. 5, no. 10, which is hereby incorporated by reference in its entirety, a negative change in refractive index in a Johnson & Johnson Acuvue 2 contact lens material of about −0.03 or more has been measured.

In an exemplary aspect, the irradiated regions of an optical, polymeric material can be defined by two- or three-dimensional structures providing the desired wavefront cross-section profile. The two- or three-dimensional structures can comprise an array of discrete cylinders, a series of lines, or a combination of an array of cylinders and a series of lines. Moreover, the two- or three-dimensional structures can comprise area or volume filled structures, respectively. These area or volume filled structures can be formed by continuously scanning the laser at a constant or varying scan rate over a selected region of the polymeric material.

In one aspect, the refractive structures may be formed proximate to the top anterior surface of an intraocular lens. For example, a positive or negative lens element (three-dimensional) is formed within a 300 μm volume, or within a 100 μm volume, from the anterior surface of the lens. The term "anterior surface" is the surface of the lens that faces the anterior chamber of a human eye. The structures may be formed at depths measured from the anterior surface of the lens or the cornea of up to 400 microns, and more preferably less than 300 microns, or less than 200 microns, but typically more than 50 microns from the anterior surface.

Figure 2:
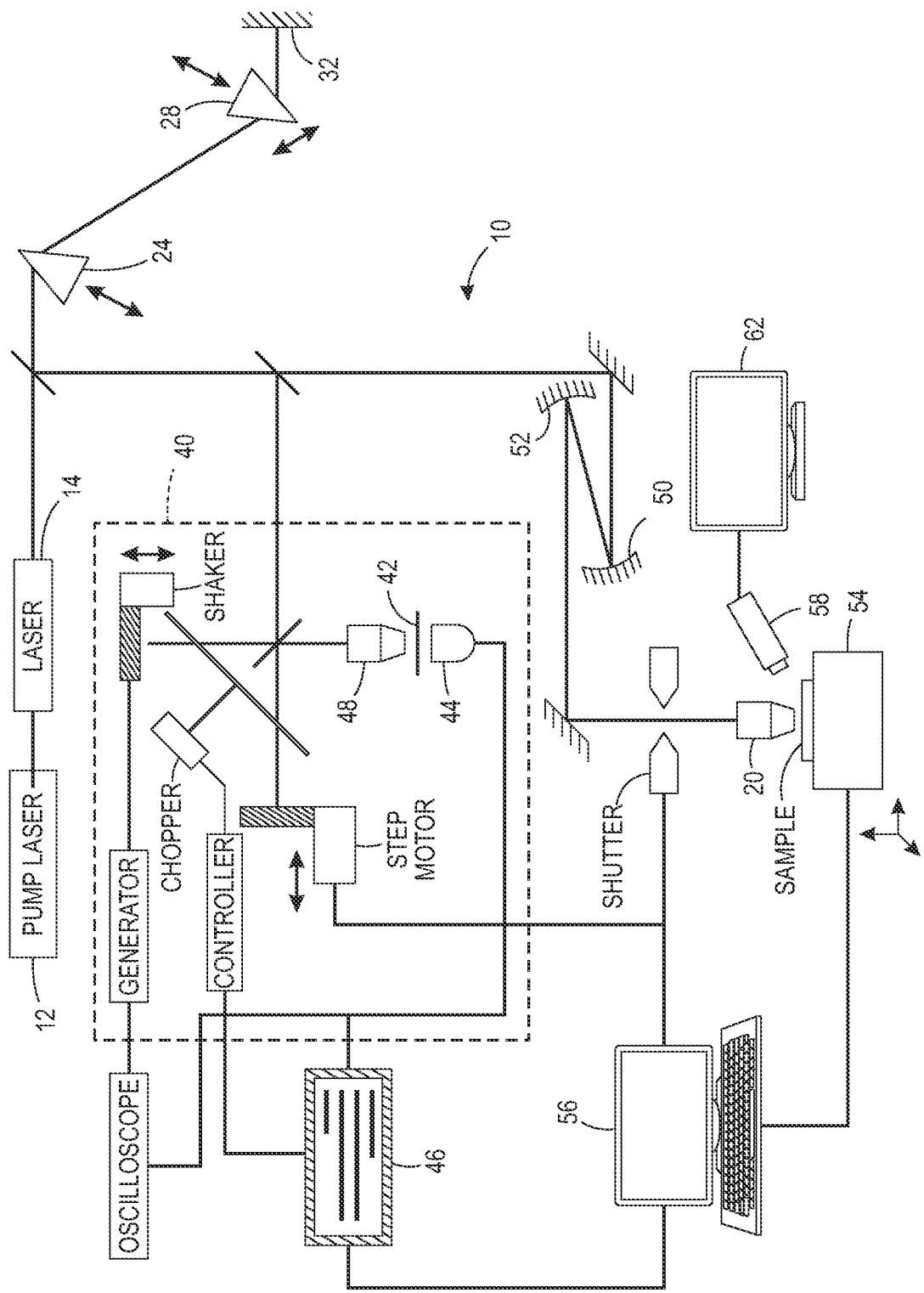
FIG. 2 shows an embodiment of a laser system that may be used in the present disclosure.

A non-limiting embodiment of a laser system 10 which may be used for irradiating an optical, polymeric material with a laser to modify the refractive index of the material in select regions to form a refractive corrector having a wavefront cross-section phase profile as described herein is illustrated in FIG. 2. A laser source comprises a Kerr-lens mode-locked Ti:Sapphire laser 12 (Kapteyn-Murnane Labs, Boulder, Colo.) pumped by 4 W of a frequency-doubled Nd:YVO4 laser 14. The laser generates pulses of 300 mW average power, 30 fs pulse width, and 93 MHz repetition rate at wavelength of 800 nm. Because there is a reflective power loss from the mirrors and prisms in the optical path, and in particular from the power loss of the objective 20, the measured average laser power at the objective focus on the material is about 120 mW, which indicates the pulse energy for the femtosecond laser is about 1.3 nJ. More recent examples have achieved greater than 200 mW average laser power at the objective focus, and in some cases greater than 500 mW. Alternative embodiments may be similar to this system, except with a laser producing 1030-1040 nm wavelengths.

Due to the limited laser pulse energy at the objective focus, the pulse width must be preserved so that the pulse peak power is strong enough to exceed the nonlinear absorption threshold of the materials. Because a large amount of glass inside the focusing objective significantly increases the pulse width due to the positive dispersion inside of the glass, an extra-cavity compensation scheme is used to provide the negative dispersion that compensates for the positive dispersion introduced by the focusing objective. Two SF10 prisms 24 and 28 and one ending mirror 32 form a two-pass, one-prism-pair configuration. In a particular instance, a 37.5 cm separation distance between the prisms is used to compensate for the positive dispersion of the microscope objective and other optics within the optical path.

A collinear autocorrelator 40 using third-order harmonic generation is used to measure the pulse width at the objective focus. Both 2nd and 3rd harmonic generation have been used in autocorrelation measurements for low NA or high NA objectives. Third-order surface harmonic generation (THG) autocorrelation may be used to characterize the pulse width at the focus of the high-numerical aperture (NA) objectives because of its simplicity, high signal to noise ratio, and lack of material dispersion that second harmonic generation (SHG) crystals usually introduce. The THG signal is generated at the interface of air and an ordinary cover slip 42 (Corning No. 0211 Zinc Titania glass), and measured with a photomultiplier 44 and a lock-in amplifier 46. After using a set of different high-numerical-aperture objectives and carefully adjusting the separation distance between the two prisms and the amount of glass inserted, a transform-limited 27 fs duration pulse is used, which is focused by a 60×0.70 NA Olympus LUCPlanFLN long-working-distance objective 48.

Because the laser beam will spatially diverge after it comes out of the laser, a concave mirror pair 50 and 52 is added into the optical path in order to adjust the dimension of the laser beam so that the laser beam can optimally fill the objective aperture. A 3D 100 nm resolution DC servo motor stage 54 (Newport VP-25XA linear stage) and a 2D 0.7 nm resolution piezo nanopositioning stage (PI P-622.2CD piezo stage) are controlled and programmed by a computer 56 as a scanning platform to support and locate the samples. The servo stages have a DC servo-motor so they can move smoothly between adjacent steps. An optical shutter controlled by the computer with 1 ms time resolution is installed in the system to precisely control the laser exposure time. With customized computer programs, the optical shutter could be operated with the scanning stages to micromachine different patterns in the materials using different scanning speeds at different position or depth in the optical material, and different laser exposure times. In addition, a CCD camera 58 along with a monitor 62 is used beside the objective 20 to monitor the process in real time.

Figure 3:
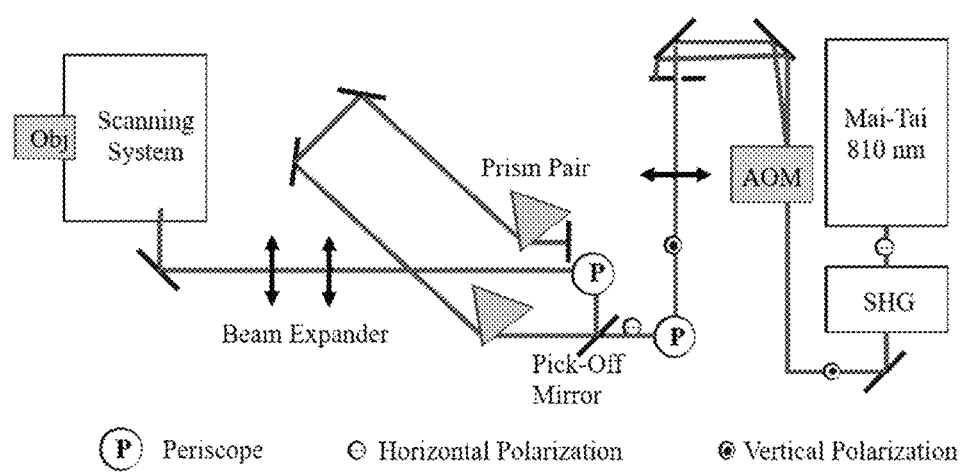
FIG. 3 shows an embodiment of a laser system that may be used in the present disclosure.

A further exemplary writing system that may be used for embodiments of the present disclosure is illustrated in FIG. 3. A frequency doubled 810 nm Ti:Sapphire laser operating a wavelength of 405 nm to create bulk optical phase change is directed through an acousto-optic modulator (AOM) in order to enable in process, fast laser power control. The AOM uses an acoustic wave to diffract a portion of the laser light into the 1" diffracted order with the amount of diffracted light dependent on the amplitude of the acoustic wave. The $0^{th}$ order, undiffracted light is blocked by an iris and the $1^{st}$ order is used as the beam for the remainder of the system. The light then passes through a pair of prisms to compensate for dispersion, producing a final pulse width of 165 fs. The beam is then directed through a beam expander to enlarge the NA. Due to thermal bloom in the prisms, the NA is laser power dependent and ranges from 0.55 at higher powers to 0.7 at lower powers. The beam then enters a scanning system designed around a custom flexure-based scanning head described in Brooks, D. R., et al., *Precision large field scanning system for high numerical aperture lenses and application to femtosecond micromachining of ophthalmic materials*. Review of Scientific Instruments, 2014. 85(6): p. 065107, with an attached water immersion objective which scans the focal region of the objective through the cornea or polymeric material lens. The flexure stage is driven using four voice coil (VC) motors. A diagram of the writing system is shown in FIG. 3.

The method and optical apparatus described above can be used to modify the refractive index of an intraocular lens following the surgical implantation of the intraocular lens in a human eye, or before the lens is implanted in an eye. Similarly, contact lenses and corneal inlays may also be altered before or after implant or application to an eye.

Accordingly, an embodiment described herein is directed to a method comprising identifying and measuring requisite vision correction for each patient, and once the vision correction is identified and quantified using methods well known in the art of ophthalmology, this information is processed by a computer. There are a number of commercially available diagnostic systems that are used to measure aberrations. For example, common wavefront sensors used today are based on the Schemers disk, the Shack Hartmann wavefront sensor, the Hartmann screen, and the Fizeau, and Twyman-Green interferometers. The Shack-Hartmann wavefront measurement system is known in the art and is described in-part by U.S. Pat. Nos. 5,849,006; 6,261,220; 6,271,914 and 6,270,221. Such systems operate by illuminating a retina of the eye and measuring the reflected wavefront.

Once the aberrations are identified and quantified, the computer programs determine the position and shape of the refractive structures to be written into the lens material to correct for those aberrations or to provide vision correction to the patient. These computer programs are well known to those of ordinary skill in the art. The computer then communicates with the laser-optical system and select regions of the lens are irradiated with a laser having a pulse energy from 0.05 nJ to 1000 nJ as described herein, to provide a wavefront cross-section phase profile comprising desired refractive features to provide desired vision correction in accordance with an embodiment of the present disclosure.

Optical, hydrogel polymeric materials that can be irradiated with a laser according to the methods described to form refractive correctors in accordance with various embodiments can be any optical, hydrogel polymeric material known to those of ordinary skill in the polymeric lens art, particularly those in the art familiar with optical polymeric materials used to make intraocular lenses or contact lenses. Broadly, non-limiting examples of such materials include those used in the manufacture of ophthalmic devices, such as siloxy-containing polymers, acrylic, hydrophilic or hydrophobic polymers or copolymers thereof—even though some of these hydrophobic materials may not typically be called hydrogels, they are included here and IRIS applies to such materials similarly, even if the refractive index changes may be different or less. The forming of the refractive structures is particularly suited for modifying the refractive index in select and distinct regions of a polymeric, optical silicone hydrogel, or a polymeric, optical non-silicone hydrogel.

The term "hydrogel" refers to an optical, polymeric material that can absorb greater than 10% by weight water based on the total hydrated weight. In fact, many of the optical, hydrogel polymeric materials will have a water content greater than 15% or greater than 20%. For example, many of the optical, hydrogel polymeric materials will have a water content from 15% to 60% or from 15% to 40%.

The optical, hydrogel polymeric materials are of sufficient optical clarity, and will have a relatively high refractive index of approximately 1.40 or greater, particularly 1.48 or greater. Many of these materials are also characterized by a relatively high elongation of approximately 80 percent or greater.

In one embodiment, the optical polymeric materials are prepared as a copolymer from at least three monomeric components. The first monomeric component, preferably a monomeric component with aromatic functionality, is present in the copolymer in an amount of at least 60% by weight, and its homopolymer will have a refractive index of at least 1.50, particularly at least 1.52 or at least 1.54. The second monomeric component, preferably, an alkyl(meth)acrylate, is present in the copolymer in an amount from 3% to 20% or from 3% to 10%, by weight. The first and second monomeric components together represent at least 70% by weight of the copolymer. The term "homopolymer" refers to a polymer that is derived substantially completely from the respective monomeric component. Minor amounts of catalysts, initiators, and the like can be included, as is conventionally the case, in order to facilitate the formation of the homopolymer.

Particularly useful first monomeric components include styrene, vinyl carbazole, vinyl naphthalene, benzyl(meth)acrylate, phenyl(meth)acrylate, naphthyl(meth)acrylate, 2-phenoxyethyl(meth)acrylate, 2,3-dibromopropyl-(meth)acrylate and any one mixture thereof. Particularly useful second monomeric components include n-butyl(meth)acrylate, n-hexyl(meth)acrylate, 2-ethylhexyl-(meth)acrylate, 2-ethoxyethyl(meth)acrylate, 2,3-dibromopropyl(meth)acrylate, 1,1-dihydroperfluorobutyl(meth)acrylate and any one mixture thereof.

The third monomeric component is a hydrophilic monomeric component. The hydrophilic component is present in an amount, from 2% to 30% by weight of the copolymer. The hydrophilic component is particularly present in an amount of less than about 20% by weight of the copolymer. Copolymers that include about 10% by weight or more of a hydrophilic monomeric component tend to form hydrogels if placed in an aqueous environment. The term "hydrophilic monomeric component" refers to compounds that produce hydrogel-forming homopolymers, that is, homopolymers which become associated with at least 25% of water, based on the weight of the homopolymer, if placed in contact with an aqueous solution.

Specific examples of useful hydrophilic monomeric components include N-vinyl pyrrolidone; hydroxyalkyl (meth)acrylates such as 2-hydroxyethyl (meth)acrylate, 3-hydroxypropyl (meth)acrylate, 2-hydroxypropyl (meth)acrylate, 4-hydroxybutyl (meth)acrylate, 2,3-dihydroxypropyl (meth)acrylate and the like; acrylamide; N-alkyl acrylamides such as N-methyl acrylamide, N-ethyl acrylamide, N-propyl acrylamide, N-butyl acrylamide and the like; acrylic acid; methacrylic acid; and the like and any one mixture thereof.

In another embodiment, the optical polymeric materials are prepared as a copolymer from at least two monomeric components and a photosensitizer. The photosensitizer can be polymerizable or be entrapped within the formed polymer. The first monomeric component is a hydrophilic monomeric component. The hydrophilic component is present in an amount from 50% to 90% by weight of the copolymer. The hydrophilic component is particularly present in an amount of 60% to 85% by weight of the copolymer. The second monomeric component, preferably, an alkyl(meth)acrylate, is present in the copolymer in an amount from 5% to 20% or from 3% to 10%, by weight. The first and second monomeric components together represent at least 90% by weight of the copolymer.

The polymeric optical materials will likely include a crosslink component that can form crosslinks with at least the first or the second monomeric components. Advantageously, the crosslink component is multi-functional and can chemically react with both the first and second monomeric components. The crosslink component is often present in a minor amount relative to the amounts of the first and second monomeric components. Particularly, the crosslink component is present in a copolymer in an amount of less than about 1% by weight of the copolymer. Examples of useful crosslink components include ethylene glycol dimethacrylate, propylene glycol dimethacrylate, ethylene glycol diacrylate and the like and mixtures thereof.

In one aspect, the optical, polymeric materials can be prepared from one or more aromatic (meth)acrylate monomers having the formula:

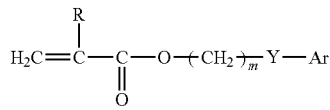

wherein: R is H or CH3; m is an integer selected from 0 to 10; Y is nothing, O, S, or NR1, wherein R1 is H, CH3, C2-C6 alkyl, iso-OC3H7, phenyl or benzyl; Ar is any aromatic ring, e.g., phenyl, which can be unsubstituted or substituted with H, CH3, C2H5, n-C3H7, iso-C3H7, OCH3, C6H11, Cl, Br, phenyl or benzyl; and a crosslinking component.

Exemplary aromatic (meth)acrylate monomers include, but are not limited to: 2 ethylphenoxy (meth)acrylate, 2-ethylthiophenyl (meth)acrylate, 2-ethylaminophenyl (meth)acrylate, phenyl-(meth)acrylate, benzyl (meth)acrylate, 2-phenylethyl (meth)acrylate, 3 phenylpropyl-(meth)acrylate, 4-phenylbutyl (meth)acrylate, 4-methylphenyl (meth)acrylate, 4 methylbenzyl (meth)acrylate, 2-2-methylphenylethyl (meth)acrylate, 2-3-methylphenylethyl (meth)acrylate, 2-4-methylphenylethyl (meth)acrylate, 2-(4-propylphenyl)ethyl (meth)acrylate, 2 (4-(1-methylethyl)phenyl)ethyl methacrylate, 2-(4-methoxyphenyl)ethyl methacrylate and the like.

Generally, if the optical, polymeric material is prepared with both an aromatic acrylate and an aromatic methacrylate as defined by the formula above, the materials will generally comprise a greater mole percent of aryl acrylate ester residues than of aryl methacrylate ester residues. It is preferred that the aryl acrylate monomers constitute from about 20 mole percent to about 60 mole percent of the polymer, while the aryl methacrylate monomers constitute from about 5 mole percent to about 20 mole percent of the polymer. Most advantageous is a polymer comprising about 30-40 mole percent 2-phenylethyl acrylate and about 10-20 mole percent 2-phenylethyl methacrylate. Hydrophilic monomer is also present in about 20-40 mole percent.

In another aspect, the optical, polymeric materials will have a fully hydrated (equilibrium) water content from 5% to 15% by weight, which also helps to minimize the degree of hazing following thermal stress as described, as well as minimize the formation of water vacuoles in-vivo. To achieve the desired water content, one may include a hydrophilic, aromatic monomer having a formula, G-D-Ar, wherein Ar is a C6-C14 aromatic group having a hydrophilic substituent, in the polymerizable compositions. D is a divalent linking group, and G is a polymerizable ethylenic site.

One particular hydrophilic aromatic monomer is represented by the formula

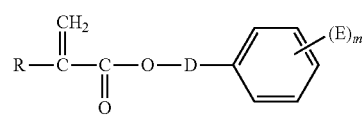

wherein R is hydrogen or CH3; D is a divalent group selected from the group consisting of straight or branched C1-C10 hydrocarbons and an alkyleneoxide (e.g., —(CH2CH2O)n-), and E is selected from the group consisting of hydrogen (if D is alkyleneoxide), carboxy, carboxamide, and monohydric and polyhydric alcohol substituents. Exemplary hydrophilic substituents include, but are not limited to, —COOH, —CH2-CH2OH, —(CHOH)2CH2OH, —CH2-CHOH—CH2OH, poly(alkylene glycol), —C(O)O—NH2 and —C(O)—N(CH3)2.

Exemplary hydrophilic, aromatic monomers are represented by the following

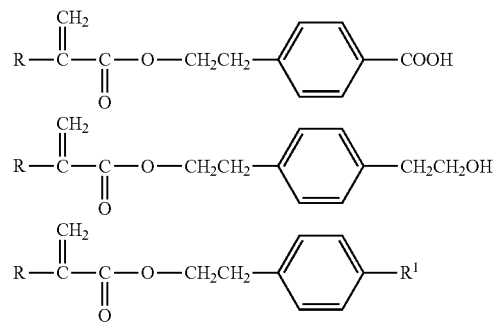

wherein R is hydrogen or CH3 and R1 is —C(O)O—NH2 or —C(O)—N(CH3)2.

In another aspect, the optical, polymeric material is prepared from a first aromatic monomeric component, which is present in 5-25% by weight, the second monomeric component is a hydrophilic monomeric component, e.g., 2-hydroxyethyl (meth)acrylate, which is present from 30 to 70% by weight; and 5 to 45% by weight of a another alkyl (meth)acrylate selected from the group consisting of methyl (meth)acrylate, ethyl (meth)acrylate, propyl (meth)acrylate, butyl (meth)acrylate, pentyl (meth)acrylate, hexyl meth) acrylate, heptyl (meth)acrylate, nonyl (meth)acrylate, stearyl meth)acrylate, octyl (meth)acrylate, decyl (meth) acrylate, lauryl (meth)acrylate, pentadecyl (meth)acrylate and 2-ethylhexyl (meth)acrylate. Among the alkyl (meth) acrylates, those containing 1 to 3 carbon atoms of alkyl group are particularly advantageous.

Exemplary aromatic monomeric components include ethylene glycol phenyl ether acrylate (EGPEA), poly(ethylene glycol phenyl ether acrylate) (polyEGPEA), phenyl methacrylate, 2-ethylphenoxy methacrylate, 2-ethylphenoxy acrylate, hexylphenoxy methacrylate, hexylphenoxy acrylate, benzyl methacrylate, 2-phenylethyl methacrylate, 4-methylphenyl methacrylate, 4-methylbenzyl methacrylate, 2-2-methyphenylethyl methacrylate, 2-3-methylphenylethyl methacrylate, 2-4-methylphenyl ethyl methacrylate, 2-(4-propylphenyl)ethyl methacrylate, 2-(4-(1-methylethyl)pheny)ethyl methacrylate, 2-(4-methoxyphenyl)ethylmethacrylate, 2-(4-cyclohexylpheny)ethyl methacrylate, 2-(2-chlorophenyl)ethyl methacrylate, 2-(3-chlorophenyl)ethyl methacrylate, 2-(4-chlorophenyl)ethyl methacrylate, 2-(4-bromophenyl)ethyl methacrylate, 2-(3-phenylphenyl)ethyl methacrylate, 2-(4-phenylphenyl)ethyl methacrylate), 2-(4-benzylphenyl)ethyl methacrylate, and the like, including the corresponding methacrylates and acrylates, and including mixtures thereof. EGPEA and polyEGPEA are two of the more preferred first monomeric components.

In another aspect, the optical, polymeric material is prepared from a hydrophilic acrylic that comprises about 90% (by weight) N-vinylpyrrolidone (NVP) and about 10% (by weight) 4-t-butyl-2-hydroxycyclohexyl methacrylate. This methacrylate hydrogel can absorb about 80% (by weight) water because of the high percentage of NVP. Its refractive index when hydrated is very close to the index of water. Another hydrophilic acrylic of interest is referred to as HEMA B, which is a poly(2-hydroxyethyl methacrylate) cross-linked with about 0.9% (by weight) of ethylene glycol dimethacrylate ("EGDMA"). This HEMA-hydrogel can absorb about 37% (by weight) water.

One particular hydrophilic, acrylic material of interest is based upon a commercially available IOL sold in the market by Bausch & Lomb under the trade name Akreos®. This acrylic material comprises about 80% by weight HEMA and 20 wt % MMA.

The optical, polymeric material can also be prepared by copolymerizing a specific monomer mixture comprising perfluorooctylethyloxypropylene (meth)acrylate, 2-phenylethyl (meth)acrylate, an alkyl (meth)acrylate monomer having the following general formula,

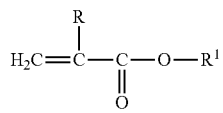

wherein R is hydrogen or methyl and R1 is a linear or branched C4-C12 alkyl group, hydrophilic monomer and a crosslinking monomer. An exemplary list of alkyl (meth) acrylate monomer include n-butyl acrylate, isobutyl acrylate, isoamyl acrylate, hexyl acrylate, 2-ethylhexyl acrylate, octyl acrylate, isooctyl acrylate, decyl acrylate, isodecyl acrylate, and the like.

The perfluorooctylethyloxypropylene (meth)acrylate is present from 5% to 20% by weight, the 2-phenylethyl (meth)acrylate is present from 20% to 40% by weight, the alkyl (meth)acrylate monomer is present from 20% to 40% by weight, the hydrophilic monomer is present from 20% to 35%, and the crosslinking agent is present from 0.5% to 2% by weight.

The optical, polymeric component will likely include a crosslinking agent. The copolymerizable crosslinking agent(s) useful in forming the copolymeric material include any terminally ethylenically unsaturated compound having more than one unsaturated group. Particularly, the crosslinking agent includes a diacrylate or a dimethacrylate. The crosslinking agent may also include compounds having at least two (meth)acrylate and/or vinyl groups. Particularly advantageous crosslinking agents include diacrylate compounds.

The optical, polymeric materials are prepared by generally conventional polymerization methods from the respective monomeric components. A polymerization mixture of the monomers in the selected amounts is prepared and a conventional thermal free-radical initiator is added. The mixture is introduced into a mold of suitable shape to form the optical material and the polymerization initiated by gentle heating. Typical thermal, free radical initiators include peroxides, such as benzophenone peroxide, peroxycarbonates, such as bis-(4-t-butylcyclohexyl) peroxydicarbonate, azonitriles, such as azobisisobytyronitrile, and the like. A particular initiator is bis-(4-t-butylcyclohexyl) peroxydicarbonate (PERK). Alternatively, the monomers can be photopolymerized by using a mold which is transparent to actinic radiation of a wavelength capable of initiating polymerization of these acrylic monomers by itself. Conventional photoinitiator compounds, e.g., a benzophenone-type photoinitiator, can also be introduced to facilitate the polymerization.

Without exclusion as to any lens materials or material modifications, e.g., the inclusion of a photosensitizer, or laser parameters described herein above, the foregoing disclosed techniques and apparatus can be used to modify the refractive properties, and thus, the dioptric power, of an optical polymeric material, typically, an optical hydrogel material, in the form of, but not limited to, an IOL, a contact lens or corneal inlay, by creating (or machining) a refractive structure with a gradient index in one, two or three dimensions of the optical material, as more fully described in U.S. Publication Nos. 2012/0310340 and 2012/0310223, incorporated by reference herein. The gradient refractive structure can be formed by continuously scanning a continuous stream of femtosecond laser pulses having a controlled focal volume in and along at least one continuous segment (scan line) in the optical material while varying the scan speed and/or the average laser power, which creates a gradient refractive index in the polymer along the segment. Accordingly, rather than creating discrete, individual, or even grouped or clustered, adjoining segments of refractive structures with a constant change in the index of refraction in the material, a gradient refractive index is created within the refractive structure, and thereby in the optical material, by continuously scanning a continuous stream of pulses. As described in greater detail in U.S. Publication No. 2012/0310340, since the refractive modification in the material arises from a multiphoton absorption process, a well-controlled focal volume corrected for spherical (and other) aberrations will produce a segment having consistent and, if desired, constant depth over the length of the scan. As further noted, when a tightly focused laser beam consisting of femtosecond pulses at high repetition rate impinges on a material that is nominally transparent at the incident laser wavelength, there is little if any effect on the material away from the focal region. In the focal region, however, the intensity can exceed one terawatt per square centimeter, and the possibility of absorbing two or more photons simultaneously can become significant. In particular, the amount of two-photon absorption can be adjusted by doping or otherwise including in the irradiated material with selected chromophores that exhibit large two-photon absorption cross-section at the proper wavelength (e.g., between 750 nm and 1100 nm), which can significantly increase the scanning speed as already described. Also, multiple segments can be written into the material in a layer using different scan speeds and/or different average laser power levels for various segments to create a gradient index profile across the layer, i.e., transverse to the scan direction. More particularly, the laser-modified GRIN layer may comprise a plurality of adjacent refractive segments having a change in the index of refraction in relation to the index of refraction of non-modified polymeric material formed with continuous streams of light pulses from a laser continuously scanned along regions of the polymeric material, wherein the plurality of adjacent refractive segments each have an independent line width and an intersegment spacing of two adjacent refractive segments is less than an average line width of the two adjacent segments so that there is overlap of the adjacent segments, and the GRIN layer is characterized by a variation in index of refraction in a direction of at least one of: (i) a transverse cross section of the adjacent refractive segments; and (ii) a lateral cross section of the refractive segments. Further, multiple, spaced gradient index (GRIN) layers can be written into the material along the z-direction (i.e., generally the light propagation direction through the material) to provide a desired refractive change in the material that corrects for some, most, or all higher order aberrations of a patient's eye. Such abilities to write continuously varying gradient index layers are particularly advantageous in forming refractive correctors having wavefront cross-section profiles in accordance with embodiments of the present disclosure. For ophthalmic applications, it is of particular interest that GRIN refractive structures are low scattering (as discussed above) and are of high optical quality.

In an illustrative aspect disclosed in U.S. Publication No. 2012/0310340, a cylindrical lens structure with a one-dimensional quadratic gradient index was written in an optical, polymeric material with three GRIN layers each 5 μm thick, spaced by 10 μm in the z-direction (i.e., a layer of non-modified optical material having a thickness of about 5 μm to 7 μm was between each two adjacent GRIN layers). The resulting cylindrical lens was designed to provide approximately 1 diopter of astigmatism uniform along the length of the device.

As further disclosed in U.S. publication No. 2012/0310223, incorporated by reference above, the femtosecond micromachining approach employed with hydrogel materials may be adapted to similarly carry out refractive correction in biological tissues by reducing the femtosecond laser pulse energies below the optical breakdown thresholds for such biological tissues, and gradient index layers may similarly be formed in such biological tissues by varying the scan rates and/or scan powers while maintaining pulse energies below such threshold energies. More particularly, refractive structures may be formed in a living eye by a method including (a) directing and focusing femtosecond laser pulses in the blue spectral region within a cornea or a lens of the living eye at an intensity high enough to change the refractive index of the cornea or lens within a focal region, but not high enough to damage the cornea or lens or to affect cornea or lens tissue outside of the focal region; and (b) scanning the laser pulses across a volume of the cornea or the lens to provide the focal region with refractive structures in the cornea or the lens. The refractive structures advantageously exhibit little or no scattering loss, which means that the structures are not clearly visible under appropriate magnification without contrast enhancement.

Induced Shape Changes

Refractive index shaping in polymer optical materials and ocular tissue by femtosecond laser writing as discussed herein can further produce shape changes in the materials. The present disclosure describes methods which may be further reemployed to take advantage of such shape changes, or to minimize or compensate therefor.

Ocular Tissue Examples

Seven live cat eyes (from 4 animals) received fs-laser treatment. Commonalities to all treated eyes were a patient interface with flat applanation using a 1 mm thick BK7 optical window and syringe suction. The treatment consisted of a fs-laser (405 nm wavelength, 80 MHz repetition rate) being focused into the cornea (approximately 250 um below the anterior surface) and raster scanned throughout a circular optical zone of 5 mm diameter at a linear scan speed of 220 mm/s and 0.5 um line-spacing. The treatment consisted of 3 layers spaced 20 um axially from each other. This resulted in a procedure time of approximately 18 minutes (or 6 minutes per layer). The laser beam was focused with a microscope objective with a numerical aperture of approximately 0.6. The laser had a pulse width of approximately 165 fs. Each layer was approximately 10 um thick upon visualization with ocular coherence tomography (OCT).

The shape of the wavefront pattern varied for each treated eye. One eye received a flat, "piston" wavefront which was of uniform laser power (150 mW) across the entire optical zone. The remaining eyes received saturated, "flat-top" Fresnel lens wavefronts where the majority of deposited laser pattern was at the maximum power of 300 mW. The saturated Fresnel lenses were saturated at approximately 30% of the un-saturated Fresnel lens height. Cross-sections of a conventional and a saturated Fresnel lens are illustrated in FIG. 4. Saturated Fresnel lenses ranged in ring patterns associated with lenses ranging from −6 to +2 diopters. However, in all of the saturated Fresnel lens patterns, the majority of the treated area had a wavefront that was flat, at the saturated (300 mW) value, resulting in a circular pattern with uniform treatment more typically over 90% of the treated circular optical zone.

The change in shape in the treated cornea was captured 3 ways. OCT was used to measure the corneal thickness and anterior corneal curvature. FIG. 5 qualitatively shows OCT corneal cross-sections of pre- and post-treatment of one of the saturated Fresnel lens cat-eyes. Note the decrease in thickness of the post-treatment image (and thus decrease in curvature and corneal focusing power (D)).

OCT was used to quantify the change in corneal curvature (as measured in corneal power (D)) as well (FIG. 6). Because this OCT method is inherently prone to noise, a Shack-Hartmann wavefront sensor was also used to more accurately quantify the change in the cat eye's wavefront aberrations. Data in FIG. 7 represents the average changes in wavefront measured with the Shack-Hartmann Wavefront sensor for each cat eye for up to over one year of follow-up.

An example time-course plot for a single eye as measured with the Shack-Hartmann Wavefront sensor is shown in FIG. 8, showing excellent stability over a one year period.

Ex-vivo studies were also performed with laser writing in enucleated rabbit eyes, using laser writing parameters similar to those described for the in vivo cat eye examples. However, a corneal topographer (Zeiss ATLAS9000) was used to quantify the change in corneal curvature. This tool was selected because it isolates the change in ocular aberrations to the anterior corneal shape and is more accurate than OCT for this application. Results showing a similar change in corneal curvature (as measured in change in Diopters) are shown in FIG. 9 for three different rabbit eyes.

For the ex-vivo experiments, the rabbit eyes were inflated with a syringe of saline solution and ocular pressure was monitored in-situ with a pressure gauge, as shown in FIG. 10. Several control experiments were performed to establish minimal effect on measured corneal curvature from intraocular pressure variations, applanation with the patient interface and alignment with the corneal topographer.

The laser treatment for the ex-vivo rabbit eyes was similar in many respects to the in-vivo cat eye experiments. There was a similar patient interface (flat applanation). The treatment was also done with a 405 nm fs-laser (80 MHz, 165 fs pulsewidth, 0.5 um line-spacing, 220 mm/s scan speed, 5 mm diameter optical zone, ~0.6 numerical aperture, 250 um depth of treatment). As shown in FIG. 9, there was one piston wavefront eye (150 mW) and 2 saturated Fresnel lens eyes (both at 300 mW max power, akin to FIG. 4). These were also 3 layer treatments with 20 um axial separation. The Fs-laser treatment clearly had the affect of flattening the central cornea, as shown by the corneal topography and corresponding power map images in FIG. 11. A central flattening corresponds to a myopia correction. Alternately, the flattening may be in an annular zone or ring towards the outside of the treatment zone, i.e. in the peripheral cornea (e.g., between 3 microns and 6 microns radially from the center of the cornea), which flattening in such peripheral annulus may effect a hyperopic correction by flattening the periphery and affecting a relative increased curvature in the central cornea.

To reduce treatment time, additional ex-vivo rabbit eyes were treated with slightly higher scan speed (300 mm/s) and broader line-spacing (2 and 5 um). FIG. 12 shows the dependency of line-spacing (i.e. treatment duration and energy dose) on the change in corneal flattening.

The above described in vivo cat eye and ex vivo rabbit eye experiments demonstrate that femtosecond laser writing parameters may be controlled to induce shape change in the cornea in addition to the previously demonstrated refractive index changes which are obtained in the cornea as a result of such femtosecond laser exposures. In particular, in accordance with one embodiment, a wavefront pattern may be written in the cornea (e.g., a human cornea) over all or the majority of an optical zone in order to induce a desired degree of thickness and/or shape change and optical power associated with such thickness or shape change over the treated optical zone. Such pattern may include a flat "piston" pattern over the desired treatment zone, or any other pattern which delivers sufficient writing power to effect the desired thickness change over the optical zone. Alternatively, patterns may be written over selected portions of the optical zone to effect shape change selectively in desired portions to partially correct for vision, or provide other desired effects associated with shape change. In all cases, however, effect of the resulting refractive index change in the treated cornea material will be taken into account, particularly when writing patterns selectively over only portions of the optical zone. Refractive index change layers to effect various optical effects may be interspersed with or below layers that are primarily for shape change effects. Alternatively or additionally, refractive index change layers and shapes may be part of the shape change layers. The refractive index change effects may be additive to or subtractive from shape change effects, and/or the refractive index change effects and the shape change effects may address different optical effects, such as add spherical add, astigmatism, multifocality (e.g., a multifocal diffractive pattern), extended depth of focus and/or higher order aberrations.

While refractive index change layers may be written at any depth in the cornea tissue from the anterior surface, the depth may be selected to provide a desired degree of shape change, as layers written closer to the anterior surface are believed to be able to provide a greater shape change effect. In a particular embodiment, e.g., a layer designed to primarily effect a desired shape change (e.g., a flat pattern) may be written in one or more layers closer to the anterior surface (for example, within 400 microns of the anterior surface, or more preferably within 300 microns, or less than 200 microns of the anterior surface of the cornea), where such written layer will have a greater effect on shape change than if written further from the anterior surface, while additional one or more layers with patterns designed to provide primarily refractive index change features (e.g., GRIN layers and/or Fresnel lens layers designed to provide tailored aberration corrections) may be written further from the anterior surface, where the combination of shape change from the layers closer to the anterior surface and refractive index changes from the layers further from the anterior surface in combination provide a desired optical correction.

In some embodiments, a patient interface or applanation lens is used to flatten or stress the cornea while the laser treatment is applied to the cornea as stated herein. Typically, such applanation lens would be incorporated with a suction ring to stabilize and control the cornea from movement during the treatment. Further, such applanation lens may be flat or curved. The stressed state of the cornea and the pressure placed on it by the suction ring and applanation lens may affect the resulting shape change, and thereby may be used to enhance or control the shape change.

Laser/Process Parameters which may have an effect on inducing shape change optical tissues, and in particular corneal tissue, in various embodiments may include, e.g., wavelength, Numerical Aperture, Pulse Width, Laser Power, Repetition Rate, and Writing Depth. In certain embodiments, e.g. when employing a Ti:sapphire or fiber laser, wavelength is preferably from 400 to 1300 nm, Numerical Aperture employed is preferably 0.1 to 1.1, more typically greater than 0.2, pulse-width is preferably from 10-1000 fs, repetition rate is preferably from 1-100 MHz, line spacing is preferably from 0.01 to 100 um, scan speed is preferably from 10 to 10,000 mm/sec, laser power is preferably from 10 to 10,000 mW, optical zone diameter is preferably from 1-10 mm, preferably from 1-10 layers are written with axial separation of from 0 to 100 um, and layer thickness is preferably from 1 to 100 um. Other parameters employed may typically be generally within the other various ranges described above. Procedures and equipment used to generate the examples provided herewith are in accordance with those already described above. Also, note that the shape change layers and optical effects may be deployed separately in time from the refractive index change optical effects, or vice versa, for example to refine or correct for residual errors from the first procedure corrections.

Contact Lens Examples

Figure 13:
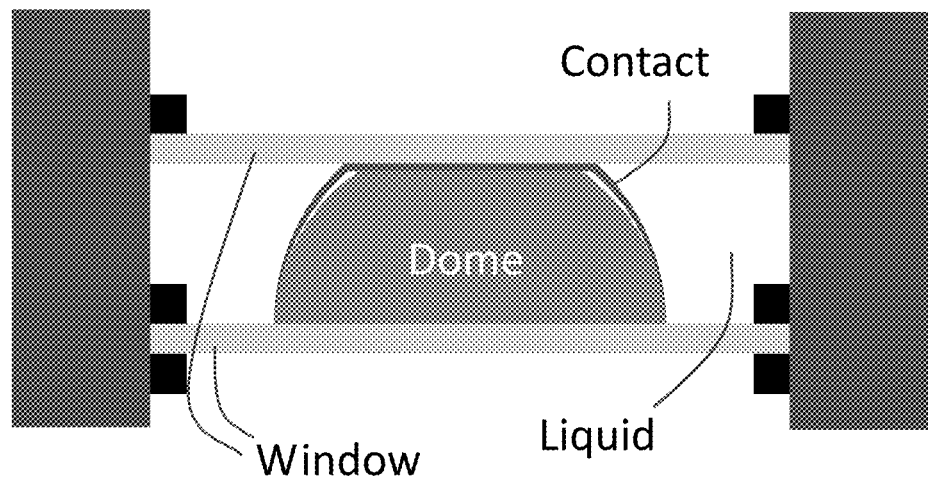
FIG. 13. Schematic of standard wet cell for applanated contact lens.
Figure 14:
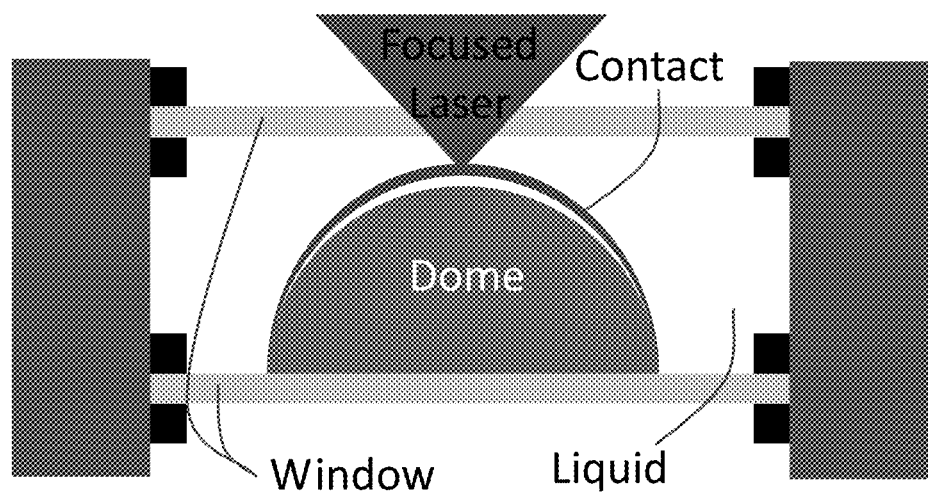
FIG. 14. Schematic of wet cell for writing in contact lens in curved configuration.

In the following contact lens examples, all examples were written in poly-HEMA hydrogels in hydrated states. Patterns were written in lenses in either a flat applanated state, or a curved, unstressed state. For flat applanated writing examples, samples were mounted in a standard wet cell and applanated using a 1 mm BK7 glass window (see FIG. 13). This creates a flat writing plane so patterns can be written by scanning in an XY plane at constant depth. For curved writing examples, a contact lens is placed on a plastic (or metal) dome which has a radius of curvature which matches the back radius of curvature of the contact lens, thus allowing the lens to rest supported in an unstressed state (see FIG. 14). A spiral pattern may then be written by X, Y and Z translation of the sample relative to the focused laser.

Optical Visual Quality of lens samples was assessed by mounting the lens in a wet cell and viewing a USAF resolution target on a custom optical bench which included a badal optometer to complete through-focus imaging.

Lenses were also imaged in profile view to evaluate any gross lens geometric changes. From the profile view, lens sagittal depth and diameter could be evaluated. Lenses were then cross-sectioned using two razor blades held back to back. Cross-sections were evaluated in a wet cell in a "free-floating" state to assess laser induced refractive index change (LIRIC) depth within the sample cross-section, surface shape changes, and cross-sectional gross shape.

Experiments have confirmed that the configuration of the hydrogel material (contact lens) during writing has a direct impact on the final shape of the lens. For contacts, gross geometrical shape changes which would affect lens on eye fitting should be avoided. Writing the lens in a flat (applanated) configuration in an XY LIRIC pattern (planar pattern) induces a stressed layer within the lens. When the lens is cross-sectioned and allowed to take the lowest energy form, the lens cross-section profile significantly deforms to reduce internal stress.

Figure 15:
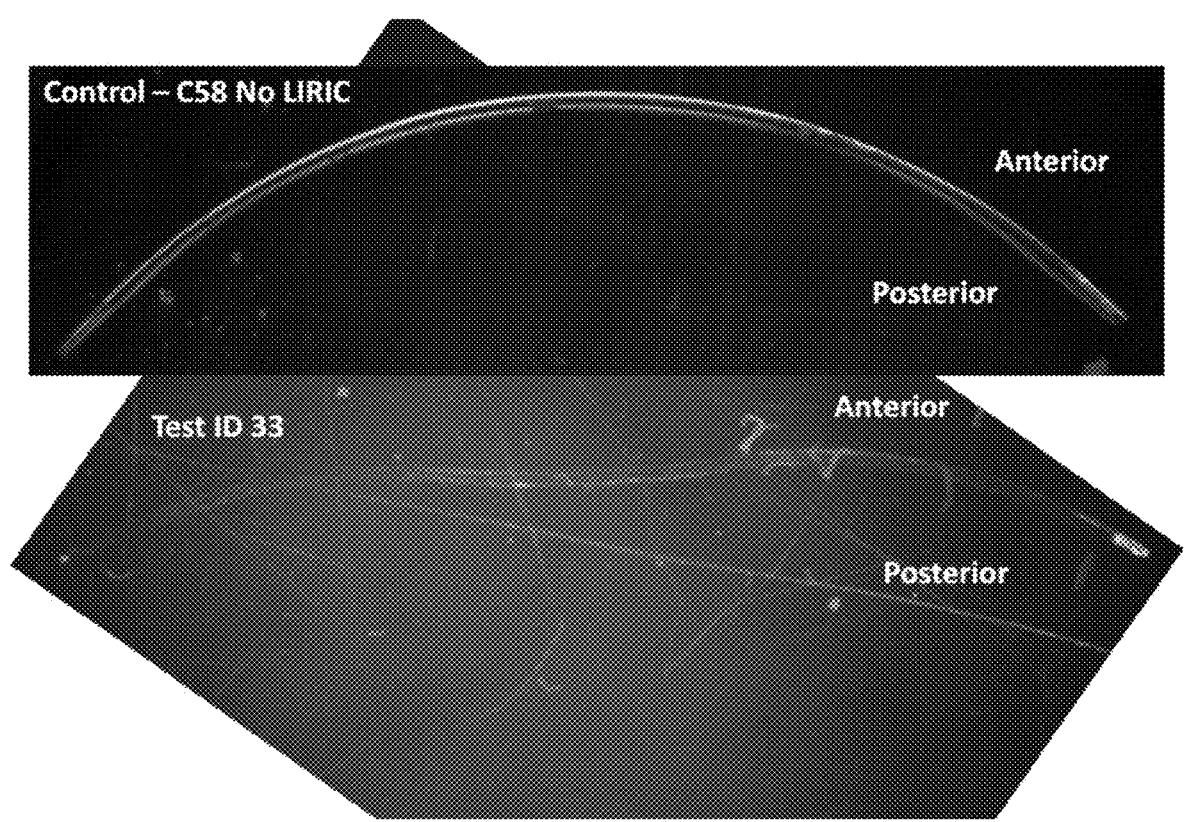
FIG. 15. (top) Un-modifed lens cross-section; (bottom) LIRIC modified lens written in applanated state FIG. 16. (top) Un-modifed lens cross-section; (bottom) LIRIC modified lens written in curved state.

FIG. 15, e.g., shows cross section images of a control lens (Contamac 58 (acofilcon A 58%) lens) on top contrasted to a LIRIC modified lens (Test ID 33) on bottom which was a Contamac 58 lens fs-laser written in a flat configuration (multifocal+2.00 D add LIRIC power gradient index Fresnel lens pattern). A fs-laser (405 nm wavelength, 80 MHz repetition rate) was employed, and raster scanned throughout a circular optical zone of 5 mm diameter at a linear scan speed of 200 mm/s. The laser beam was focused with a microscope objective with a numerical aperture of approximately 0.19. The laser had a pulse width of approximately 190 fs. Laser Power varied between 0-100 nW. Lens and writing parameters were as follows: BVP: 0.00D; LP: +2.00D; NP: 2.00D; ADD: +2.00D; D/N: 70/30; Writing depth: 80% (156 um/195 um); Writing speed: 200 mm/sec (flat). As seen in FIG. 15, the laser-writing in the lens in a flat applanated state induces stress in the lens which changes the lens shape/curvature. Where such shape changes are undesired, writing configurations which induce stress in the lens should be avoided to avoid loss of optical performance.

Figure 16:
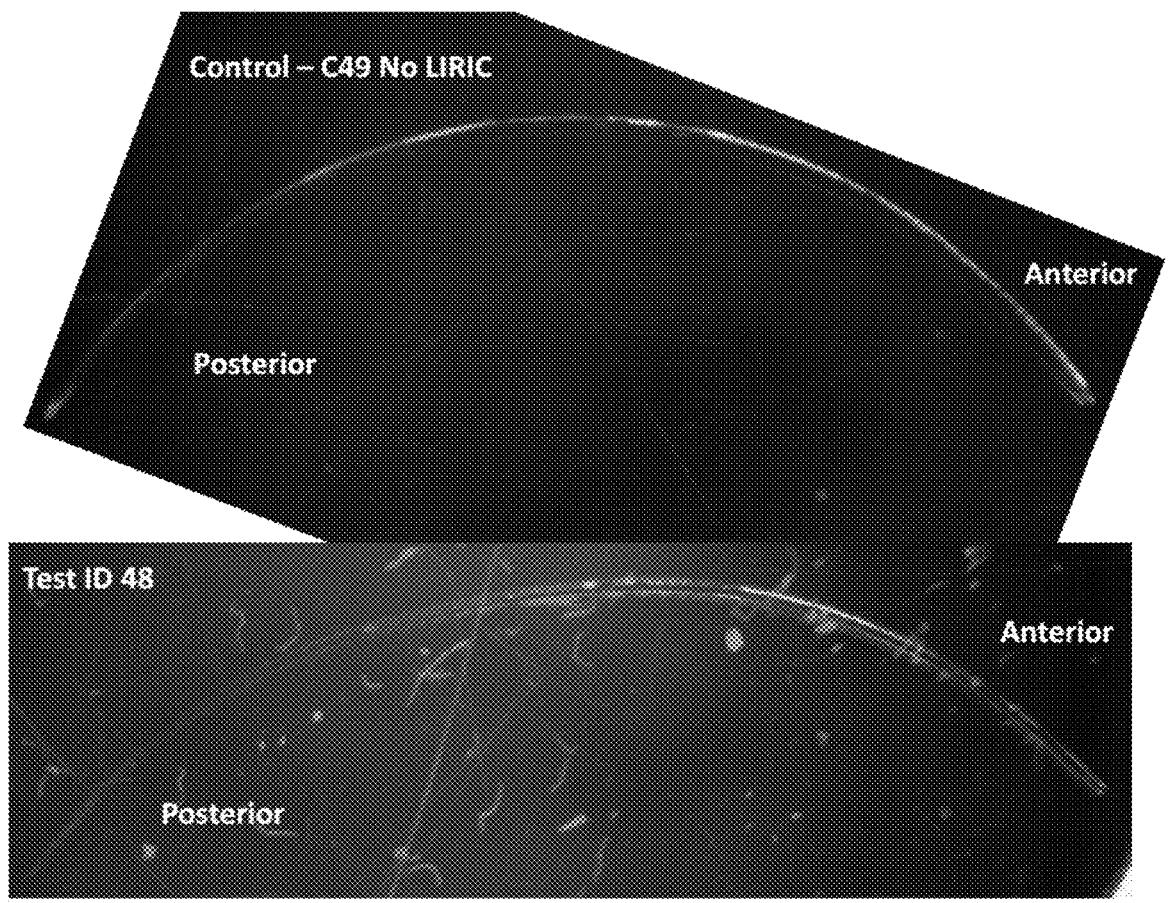

In accordance with one embodiment of the disclosure, undesired lens shape changes induced by laser writing may be reduced by maintaining the lens in a curved configuration matching the lens native shape during the LIRIC writing process, whereby internal stresses within the lenses can be avoided. FIG. 16, e.g., shows cross sectional images of a control lens (Contamac 49 (acofilcon A 49%) lens) on top contrasted to a LIRIC modified lens (Test ID 48) on bottom which was a Contamac 49 lens fs-laser written in a curved configuration (multifocal +1.25 D add LIRIC power gradient index Fresnel lens pattern). A fs-laser (405 nm wavelength, 80 MHz repetition rate) was employed, and written in a spiral pattern throughout a circular optical zone of 5 mm diameter at a scan speed of 5 mm/s. Lens and writing parameters were as follows: BVP: 0.00D; LP: +1.25D; NP: 1.25D; ADD: +1.25D; Writing depth: 60% (100 um/167 um (variable with spiral pattern)); Writing speed: 5 mm/sec (spiral). As seen in FIG. 16, the laser-writing in the lens in a curved unstressed state more closely maintains the initial lens shape/curvature after writing relative to writing in the flat applanated state as shown in FIG. 15.

While undesired shape changes may be minimized by writing in a lens in a curved, stress free state, shape changes may also be intentionally induced in a controlled manner to provide optical and/or physical effects where desired.

Shape change in hydrogel materials may be dependent, e.g., on the following parameters: Hydrogel material properties (water content, modulus), laser writing properties (wavelength, pulse width, wavefront, energy deposition (power, speed, dwell time), rep rate, Laser focal spot size (numerical aperture)), LIRIC writing pattern (# layers, layer spacing, line spacing, numerical aperture, delivered pattern, writing depth), Any one or some combination of the above parameters can be used to control the magnitude, profile, orientation or existence of shape change in hydrogel materials.

Depth—proximity to surface may influence strength of effect. Thicker samples typically exhibit less surface deformation for a given treatment. Can use depth of laser writing to control surface shape.

Wavelength—wavelength drives strength of response. Optimal wavelength will depend on the absorption properties of the material. For synthetics, this can be designed. For cornea, the response is better at higher-energy (shorter) wavelengths, but doping is a definitive way to enable use of longer wavelengths.

Pulse width—pulse width influences the efficiency of the multiphoton process and has an impact on the damage threshold. Pulse width could be varied to control strength of effect, optimize processing time, or achieve higher maximum effect sizes (both in RI change and deformation). For materials with higher damage thresholds, 250-400 fs may be preferably employed. For enabling higher process efficiency, <250 fs may be preferred.

Wavefront—wavefront may have an impact on process effect and likely has an impact on damage threshold. Wavefront also has an effect on the axial profile of the processed region and can be used to control thickness of the LIRIC region and thus the profile of the mechanical modification. This could be used to control the deformation at the surface by changing the internal structure. Increased spherical aberration (tested up to 2 um) shows an increased LIRIC response, likely due to an axial elongation (increase) of the processed region.

Power—power influences the process effect nonlinearly and can be used to drive the magnitude of surface deformation. Power has an impact on the volume of the LIRIC region. This controls the internal structure, area of increased water content and swelling, and thus surface deformation. Power parameters are typically coupled with speed, and further depends on material, wavelength, etc. For a 405 nm wavelength laser, e.g., at 200 mm/s spot translation speed, exemplary range is 0 to 300 mW. At 5 mm/s, exemplary range is 0 to 65 mW. For a 810 nm laser, at 200 mm/s spot translation speed, exemplary range is 0 to 1 W. Ranges similar between cornea and hydrogel. For a 1035 nm laser, at 2 m/s, exemplary range is 0 to 2 W.

Speed—speed influences energy deposition, and could be used to control the volume of the LIRIC region. Exemplary speeds: 405 nm: 0 to 1 m/s. 810 nm: 0 to 1 m/s. 1035 nm: 0 to 2 m/s. 2 m/s likely relevant for all materials and wavelengths. Speeds up to 10 m/s are contemplated. Maximum speed limited by required exposure limitations.

LIRIC region volume—volume of the LIRIC region (with or without a constant modulus/RI change) can be used to drive the magnitude of surface deformation. Axial volume will drive the magnitude of deformation. Cross sectional area will drive the lateral size of the affected region and thus curvature (in combination with magnitude of deformation). Relevant size: Axial—0 um to thickness of material (thinnest hydrogels -40 um; Thickest cornea -600 um). Lateral—Dependent on focal volume, typically between 0.1 um and 50 um.

Dwell time—similar to speed, influences energy deposition and thus volume of LIRIC region. Range from minimum controllable dwell (single pulse range, ns or less) up to several seconds. Depending upon focusing strategies, this could be higher (e.g., 10 s of seconds). Speed, power, and dwell time are all used to control rate of energy deposition.

Rep rate—controls peak pulse power and drives single-pulse response. Higher power pulses have a stronger response, but also may exceed the damage threshold at lower average powers, and thus have a smaller dynamic range. Exemplary range from 100 kHz to 100 MHz. Likely controls mechanism of action (thermal, photochemical). Single pulse approaches are relevant, which would represent a variable rep rate or a rep rate of "0" Hz.

Number of layers—number of layers drives the LIRIC region volume. Different LIRIC volumes could be applied on different layers to drive a complex surface shape. 0 to 100s of layers are relevant, given a very thin layer (1 um scale) and a thick sample (100s of ums).

Layer spacing—overwriting is possible. Can reprocess same area to change LIRIC region volume. Could displace layers slightly to get a spatially varying overlap and thus a spatially varying modulus change. Could displace layers completely to get independent, additive effects. Range from 0 um (overlapped completely) up to thickness of material.

Line/spot spacing—control density of LIRIC regions. Can space individual spots in a grid (uniform or non-uniform) to control shape on a point-by-point basis. Range: 0 um (overlapped) up to 10 mm (size of relevant optical zone or area required to affect optical zone).

Numerical aperture—affects focal volume, which directly influences LIRIC region volume and gradient of modulus change. Exemplary range 0.1 (possibly lower) to 1.1.

Pattern delivered—specific location of LIRIC change could be used to control the shape of the deformation at the surface. E.g., a "LIRIC spot" pattern may be written to induce refractive index change and corresponding shape change in discrete local regions of the pattern. Alternatively or additionally, circular LIRIC lines of controlled spacing may be written to induce a raidally symmetric varying LIRIC pattern and associated shape profile. Many of the described parameters can be used to control the pattern delivery. For example, the shape and size of the spots in a "LIRIC spot" diagram can be controlled by: dwell time, power, NA, wavefront, number of layers, layer spacing, depth, and rep rate.

Figure 17A:
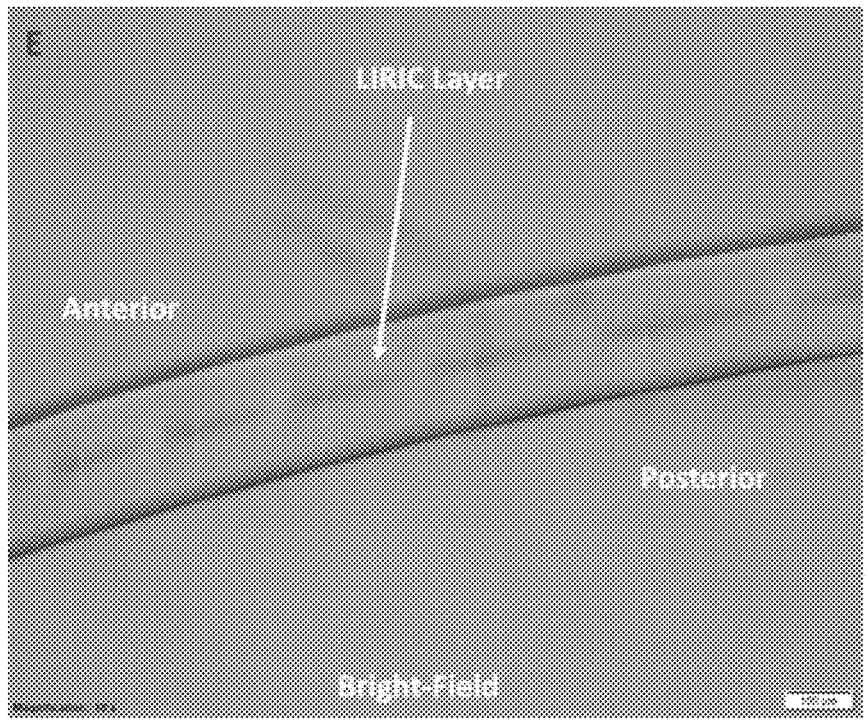
FIGS. 17A and 17B: cross sectional images of portions of a LIRIC modified lens.
Figure 17B:
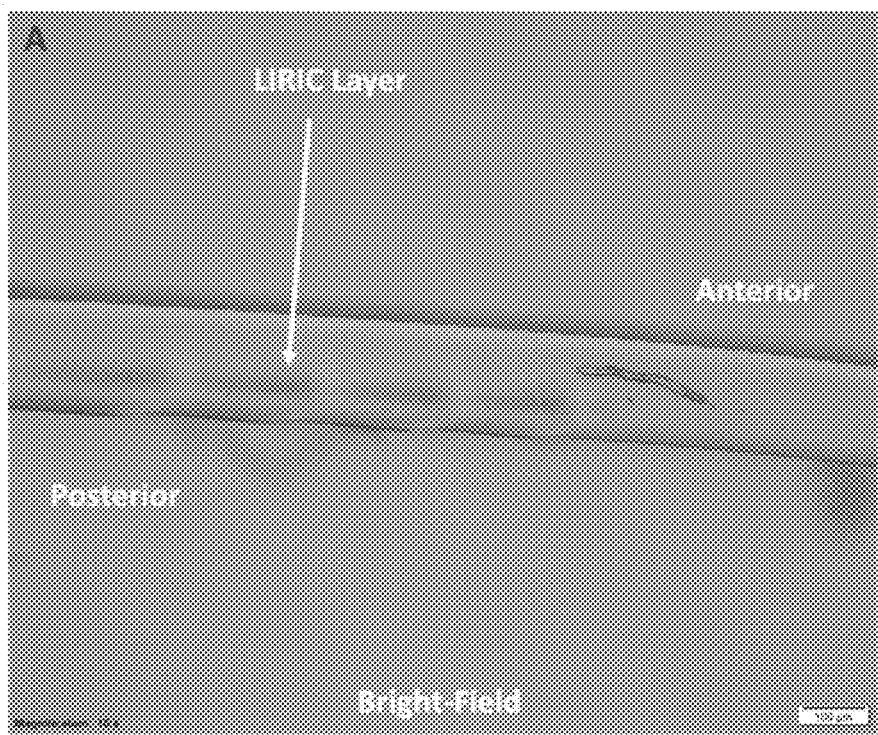

A direct relationship between proximity to a surface of a LIRIC layer and local magnitude of a surface shape change has been demonstrated. FIGS. 17A and 17B, e.g., show cross sectional images of portions of a LIRIC modified lens (Test ID 48) which was a Contamac 49 lens fs-laser written in a curved configuration (multifocal+1.25 D add LIRIC power gradient index Fresnel lens pattern). The writing of the spiral pattern resulted in sections of the LIRIC layer being written at varying depths from the surface. In FIG. 17A, the LIRIC layer was written nearer the center of the hydrogel cross-section, resulting in minimal local surface shape change at either the anterior or posterior surfaces of the hydrogel. FIG. 17B, on the other hand, depicts surface shape change when the LIRIC layer is written closer to the posterior surface of the material. Notice that the profile of the surface change is localized to the LIRIC bars.

Figure 18:
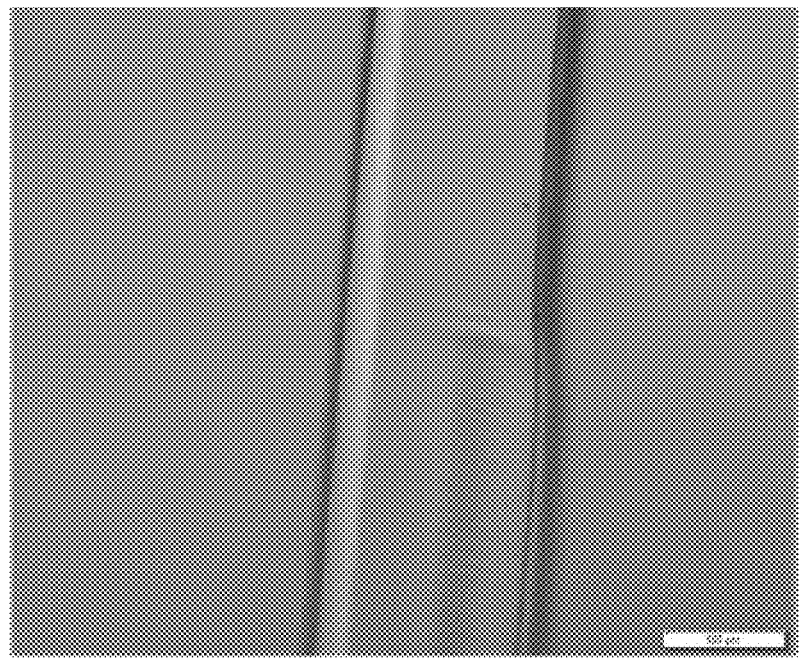
FIG. 18. Piston pattern uniform shape change.

The profile of the LIRIC pattern also has a direct relationship to the profile of the shape change. A uniform LIRIC pattern (i.e. constant pattern over a zone) as is used to generate a piston type lens results in a uniform shape change across the LIRIC modified region with a defined boundary at the LIRIC modified/unmodified region, as shown in FIG. 18 (depicts the shape change at the LIRIC boundary of a Contamac 58 lens fs-laser written in a flat configuration with a piston pattern (0.5 wvs phase change with 0.00 D add LIRIC power piston design pattern). A fs-laser (405 nm wavelength, 80 MHz repetition rate) was employed, and raster scanned throughout a circular optical zone of 5 mm diameter at a linear scan speed of 200 mm/s. The laser beam was focused with a microscope objective with a numerical aperture of approximately 0.19. The laser had a pulse width of approximately 190 fs. Lens and writing parameters were as follows: BVP: 0.00D; LP: 0.00D; NP: 0.00D; ADD: 0.00D; D/N: 0/0; Writing depth: 50% (95 um/190 um); Writing speed: 200 mm/sec (flat). Contrast to the modulating shape change in FIG. 17B resulting from a Fresnel type pattern where laser power modulates across the structure.

For shape control writing patterns, each lens material will require a tuned set of writing parameters to balance refractive index change with material modulus change. Different base materials will be more or less susceptible to gross geometrical changes based on material monomer composition, water content and material modulus. Lower modulus materials (softer materials), may be more susceptible to shape change than stiffer (higher modulus) materials.

Controlled surface bulging (e.g. in a piston type structure) could be used to modify the refractive power of a lens or induce other refractive type changes to a lens without potentially degrading the oxygen permeability of the material (this is based on the LIRIC modified region being composed primarily of water with water having a higher oxygen permeability compared to surrounding polymer).

For tuning parameters, each material will behave slightly differently, but in general shape change will be driven by the magnitude of LIRIC phase change. This is a direct result of the base material chemistry, wavelength of laser used and subsequent parameters of the laser. The base material is composed of some combination of monomers, initiators, crosslinkers, UV blockers, dye colorants and preservatives. Each one of these molecules have absorption wavelengths and potential chemical functional groups which are susceptible to chemical modification by the laser energy. Different chemical groups will behave differently to the laser energy. Combination of bond breakage and functional group modifications may result in water moving into the LIRIC modified region. The water moving into the modified region may be either free (unbound water) or bound water which may result in either transient shape change or permanent shape change. Therefore, tuning the laser wavelength to have absorption by the hydrogel and then tuning laser power, pulsewidth, rep rate, numerical aperture to control the magnitude of phase change may result in control of material shape change.

Used in concert with refractive index change, it may be possible to either correct for surface aberrations caused by the diffractive optic using an independent pattern intended solely or primarily to effect surface change. This is due to the fact that the RI change is highly localized, while the shape change is much less so. LIRIC is on the order of the size of the focal spot, a few um in cross sectional area. The shape change extends well outside of the LIRIC region, affecting material up to 100s of ums away. This could also be effected by small LIRIC regions that will have a limited effect from an optical standpoint (due to low RI or small lateral area) but may have a relatively large surface deformation effect.

Shape change may also be used to do arbitrary wavefront correction via specifically patterning LIRIC treatment. This would be particularly effective if the LIRIC regions were particularly small, thus imparting almost no optical effect from the RI change, or were a constant phase.

The descriptions provided assume hydrogel as the material being processed, unless otherwise specified. However, in cornea, it should be noted that the shape change effects may typically occur in an opposite direction (i.e., parameters that produce swelling and an increase in surface height in hydrogels may produce a decrease in surface height in cornea or IOLs).

Further on-eye testing has resulted in findings that relatively deeper LIRIC writing in thicker lenses (e.g., Acuvue+ 5.0D Base lens) has resulted in better Visual Acuity based on on-eye testing than relatively shallow LIRIC in thinner lenses (Acuvue+3.0D Base lens), evidencing less surface disruption. Also, higher induced phase change diffractive Fresnel patterns (0.57 wvs) induced in Contamac 58 Plano lenses have been found to result in worse visual acuity than lower induced phase change diffractive Fresnel patterns patterns (approx. 0.20 wvs), evidencing lower phase change also results in less surface disruption. Writing of a 0.5 wvs piston pattern in Contamac 58 Plano lenses at a depth of 80% with no add power to the lens did not significantly alter optical properties of the plano lens.

Curved Contact Lens Writing Protocol

For curved contact lens writing using LIRIC, the following steps may be employed. First, determine the relevant parameters. These include the back radius of curvature (BRC) of the contact lens (this assumes there is a corresponding mount that is the same back radius of curvature to minimize stress during writing); the radius (R) of the field to be written over; the writing offset from the back of the contact lens (dBRC) must be smaller than the contact lens thickness; the radial step size (dS) of the pattern (usually 0.5 µm); the Desired Refractive Power ($D_s$); and the Design Wavelength ($\lambda_d$) usually the middle of the visual spectrum ~543 nm.

Second, calculate the curved trajectory:

Height of curved pattern:

$Z_{max} = (BRC + dBRC) - \sqrt{(BRC + dBRC)^2 - (R)^2}$

Max angular extent: $\theta_{max} = \arctan\left(\frac{R}{BRC + dBRC - Z_{max}}\right)$ Build angular vector: $\theta = 0 : \frac{dS}{BRC + dBRC} : \theta_{max}$ Build radial, $x$, and $z$ position vectors:

-continued $r = (BRC + dBRC)\theta$ $x = (BRC + dBRC)\sin(\theta)$ $z = (BRC + dBRC)\cos(\theta) - (BRC + dBRC)$ Calculate desired phase change vector in waves (note, the squared p term is scalar, not matrix multiplication):

$$W_{\mu m} = \frac{-(R)^2(d_s)(\rho^2 - 1)}{2}$$

Third, Scale and wrap the desired Wavefront:

Scale phase change vector to waves at desired wavelength:

$$W_{\lambda_d,1} = \frac{1000 W_{\mu m}}{\lambda_d}$$

assume $\lambda_d$ is in nanometers

Subtract the first value of the wavefront vector from each other value:

$$W_{\lambda_d,2} = W_{\lambda_d,1} - W_{\lambda_d,1} \qquad (1)$$

Wrap the wavefront vector such that it is between 0 and 1 waves.

When completed, this generates a wavefront vector and two spatial coordinates.

Figure 19:
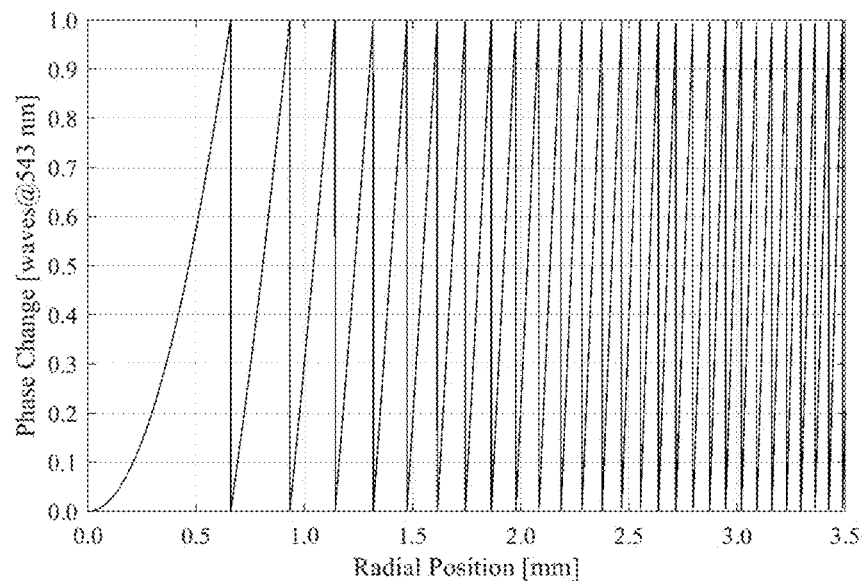
FIG. 19. Fresnel phase change pattern diagram.
Figure 20:
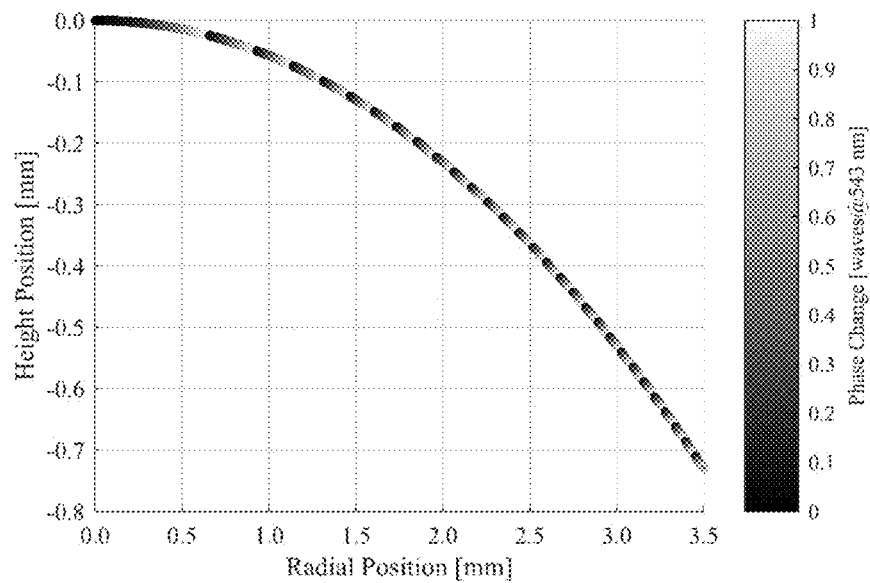
FIG. 20. Lens phase change diagram.

An Example Refractive Device calculation is provided, wherein BRC=8.5 mm, dBRC =50 µm, dS=0.5 µm, R=3.5 mm, $D_s$=+2.5 Diopters, and $\lambda_d$=543 nm. The desired Fresnel phase change pattern and lens phase change diagram are shown in FIGS. 19 and 20, respectively.

For Power Calibration, to understand the output laser power as a function of input voltage signals in the laser writing system, data points are fit to a function of form:

$$f(x) = A\left(1 - \exp\left(-\left(\frac{x}{b}\right)^c\right)\right) + D$$

Figure 21:
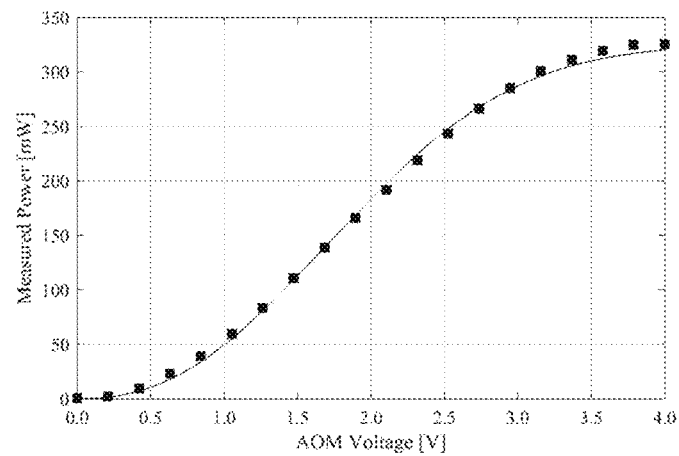
FIG. 21. Power calibration curve.

A, B, C, and D are all floating parameters. With this, generate the calibration curve for the system, which can then be calculated to find voltage values at a much finer spacing. An exemplary power calibration curve is shown in FIG. 21.

Figure 22:
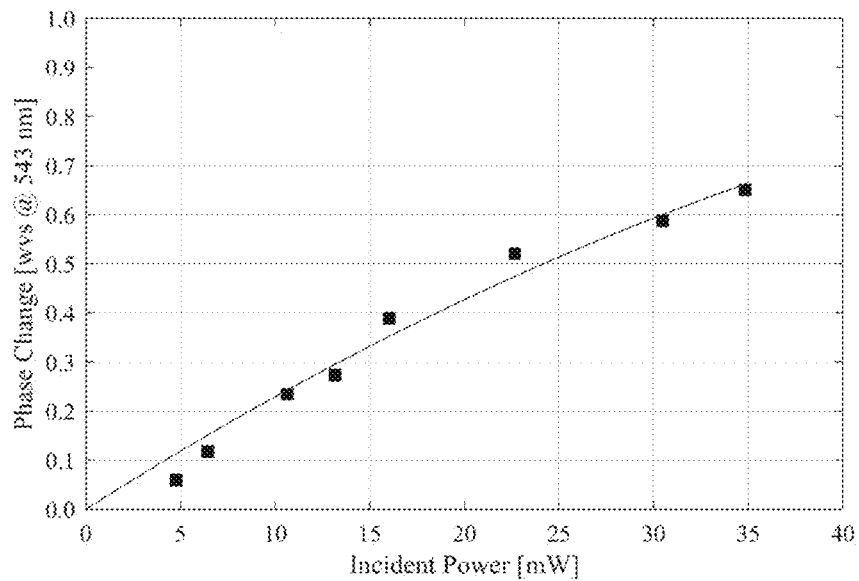
FIG. 22. Phase calibration curve.

For Phase Calibration, calibration artifacts for the system and materials may be separately generated to convert the phase calibration to a function of input power. This data may be fit to determine its functional form so the induced phase change can be estimated as a function of power. An exemplary phase calibration curve is shown in FIG. 22.

The phase change calibration curve may optionally be rescaled. There are some instances, e.g., when the phase change does not achieve 1 wave at the desired wavelength or when wanting to make a diffractive device that does not force all of the light into one order. This is often the case for multifocal lenses. For example, the curve of FIG. 22 may be rescaled to assume that it achieves 1 wave, even though these parameters will only generate ~0.7 waves.

Finally, the desired pattern, phase calibration, and power calibration may be interpolated to provide X (radius), Z (depth) and V (voltage) vectors for writing the desired pattern. Filters may be applied to the X, Y and Z axes movements such that scanning motion is smoothed and not discontinuous. By translating the scanning through X, Y and Z axis, an Archimedes spiral pattern may be written for the lens in its naturally curved state.

When used in concert with refractive index change, it may be possible to either correct for surface aberrations caused by the diffractive optic using an independent pattern intended solely to effect surface change. This is due to the fact that the RI change is highly localized, while the shape change is much less so. LIRIC is on the order of the size of the focal spot, a few um in cross sectional area. The shape change extends well outside of the LIRIC region, affecting material up to 100s of ums away. See diagram, showing possible compensation via LIRIC layer depth. This could also be effected by small LIRIC regions that will have a limited effect from an optical standpoint (due to low RI or small lateral area) but will have a large surface deformation effect.

In particular embodiments, induction of shape change and/or stress is directly affected by the mounting (shape of the optical polymeric material (e.g., lens) or ocular tissue) during writing. Writing a pattern in a lens in a relatively flat, stressed applanated state, e.g., can result in a change in resting shape of the lens when the stress is removed. Writing in a pattern in a less stressed curved state, on the other hand, can help maintain the geometry of the contact lens when in a resting state.

Laser/Process Parameters which may have an effect on inducing shape change in various embodiments may include, e.g., Numerical Aperture, Pulse Width, Laser Power, Repetition Rate, Writing Depth, and Hydrogel water content. Numerical Aperture employed is typically 0.1 to 1.1, more typically greater than 0.2, and the other parameters employed may be generally within the ranges described above. Procedures and equipment used to generate the examples provided herewith are in accordance with those already described above.

In particular embodiments, refractive structures written in an optical polymeric material or ocular tissue covering a surface area of at least about 3 mm$^2$ (e.g., circular zones having a diameter of greater than 2 mm) have been found to be more likely to generate a significant shape change in a polymeric optical lens of ocular tissue. The present disclosure is thus particularly applicable to patterns of such size and larger written in such materials, more particularly, e.g., surface areas of at least about 5 mm$^2$, or at least about 10 mm$^2$. Even more particularly, the disclosure is applicable to refractive structure patterns covering the majority of area of a circular zone of 6 mm diameter, so as to cover the majority of the clinically relevant optical zone of the eye. Patterns of refractive structures written in such materials may define particular devices, structures, or shapes. Such refractive structures may further preferably be written in the form of a Fresnel lens, so as to enable greater diopter changes, but the disclosure is also applicable to writing of non-Fresnel patterns, such as piston, cylinders, tilt wedge patterns or curved/spherical or aspheric patterns, which may work in various embodiments to effect thickness/shape changes, in addition to or in opposition to attendant refractive index changes.

In one particular embodiment, a method for modifying an optical device selected from a contact lens, intraocular lens, or corneal inlay for improving visual performance in a patient, wherein the optical device includes central optical and outer peripheral zones comprising an optical polymer material is described, comprising: modifying the refractive index of the optical polymer material by irradiating select regions with a focused, visible or near-IR laser below the optical breakdown threshold of the optical polymer material to provide refractive structures that exhibit a change in refractive index, and exhibit little or no scattering loss, and scanning over the select regions with the laser such that ablation or removal of the optical polymer material is not observed in the irradiated region, wherein the refractive structures are formed while the optical polymeric material is in a curved, relatively low-internal stress form to reduce surface shape change or distortions of the refractive structures or of the shape of the optical device which result when the structures are formed while the optical material is in a stressed applanated form. In particular, the refractive structures preferably cover the majority of area of a circular zone of 6 mm diameter, so as to cover the majority of the clinically relevant optical zone of the eye. Such refractive structures may further preferably be written in the form of a Fresnel lens, so as to enable greater diopter changes.

In a further particular embodiment, a method for modifying an optical device selected from a contact lens, intraocular lens, or corneal inlay for improving visual performance in a patient, wherein the optical device includes central optical and outer peripheral zones comprising an optical polymer material is described, comprising: modifying the refractive index of the optical polymer material by irradiating select regions with a focused, visible or near-IR laser below the optical breakdown threshold of the optical polymer material to provide refractive structures that exhibit a change in refractive index, and exhibit little or no scattering loss, and scanning over the select regions with the laser such that ablation or removal of the optical polymer material is not observed in the irradiated region, wherein the refractive structures are formed in a pattern while the optical material is in a stressed applanated form, where removal of the stress results in a change of the pattern, and wherein the pattern written while the optical material is in a stressed applanated form is designed to result in a desired pattern upon removal of the stress. In particular, the refractive structures preferably cover the majority of area of a circular zone of 6 mm diameter, so as to cover the majority of the clinically relevant optical zone of the eye. Such refractive structures may further preferably be written in the form of a Fresnel lens, so as to enable greater diopter changes, or other diffractive pattern. Upon removal of the stress, an anterior and/or posterior surface shape of the optical device may be changed. In further specific embodiments, the surface shape change may provide a change in at least one of the sphere, cylinder, multifocality or depth of focus of the optical device relative to the untreated optical device.

In a further embodiment, a method for modifying an optical device selected from a contact lens, intraocular lens, or corneal inlay for improving visual performance in a patient, wherein the optical device includes central optical and outer peripheral zones comprising an optical polymer material is described, comprising: modifying the refractive index of the optical polymer material by irradiating select regions with a focused, visible or near-IR laser below the optical breakdown threshold of the optical polymer material to provide refractive structures that exhibit a change in refractive index, and exhibit little or no scattering loss, and scanning over the select regions with the laser such that ablation or removal of the optical polymer material is not observed in the irradiated region, wherein the refractive structures are formed in a pattern which results in an overall shape change to the optical device, and wherein the shape change is employed in combination with the refractive index change to provide a desired optical correction for the device.

In such embodiment, the shape change may be dynamic resulting in gradual prescription changes over time, and the gradual prescription change may be used to control obsolescence of the optical device in accordance with a recommended optical device replacement schedule. The gradual prescription change of the optical device may further be designed to provide a gradual change to a target prescription, or to accommodate anticipated prescription changes for a patient. Further, the refractive structures preferably cover the majority of area of a circular zone of 6 mm diameter, so as to cover the majority of the clinically relevant optical zone of the eye. Such refractive structures may further preferably be written in the form of a Fresnel lens, so as to enable greater diopter changes, or other diffractive pattern. In a further embodiment, the refractive structures may be formed in a pattern in an outer peripheral region which results in a shape change to the optical device which provides a ballast function for the optical device for orienting the optical device in a wearer's eye. In specific embodiments, the refractive structures are written in the form of a saturated Fresnel lens or diffractive pattern.

In further specific embodiments, the depth of writing of the pattern may be used to directly control the amount of shape change on either surface of the optical device. More particularly, the amount of shape change may be further controlled by the width and layer thickness of the refractive structures, and/or by the number of layers of refractive structures.

In further specific embodiments, the induced shape change may be used to create ballast for a contact lens to maintain orientation on the cornea. More particularly, the created ballast may be an asymmetrical surface shape change to weight the lens on the bottom, and the ballast may be generated by a refractive structure created to counter any optical effects of that ballast surface change. Further, one refractive structure close to the anterior surface may be created to effect the ballast surface change, and another deeper layer refractive structure may be written to produce an optical effect from change of refractive index to reduce the optical effects of the ballast.

In further specific embodiments, the shape change may have the optical effect of reducing astigmatism or higher order aberrations, and/or of inducing spherical abberation to produce increased depth of focus.

In a further embodiment, a method for modifying an optical device selected from a contact lens, intraocular lens, or corneal inlay for improving visual performance in a patient, wherein the optical device includes central optical and outer peripheral zones comprising an optical polymer material is described, comprising: modifying the refractive index of the optical polymer material by irradiating select regions with a focused, visible or near-IR laser below the optical breakdown threshold of the optical polymer material to provide refractive structures that exhibit a change in refractive index, and exhibit little or no scattering loss, and scanning over the select regions with the laser such that ablation or removal of the optical polymer material is not observed in the irradiated region, wherein the refractive structures are formed in a pattern which results in an overall shape change to the optical device, and wherein the depth of writing is used to directly control the amount of shape change on either surface of the optical device. In particular embodiments, e.g., the amount of shape change may be further controlled by the width and layer thickness of the refractive structures, and/or by the number of layers of refractive structures. The refractive structures may be written at a depth from the surface of greater than 50% to reduce the amount of shape change relative when the refractive structures are written closer to the surface. The optical device may more particularly have a convex anterior surface and a concave posterior surface, and the refractive structures may be written at a depth closer to the concave posterior surface in order to reduce the shape change. The refractive structures may further be written in the optical device while the device is in an applanated form. Further, the refractive structures preferably cover the majority of area of a circular zone of 6 mm diameter, so as to cover the majority of the clinically relevant optical zone of the eye. Such refractive structures may further preferably be written in the form of a Fresnel lens, so as to enable greater diopter changes, or other diffractive pattern.

In a further embodiment, a method for modifying visual performance in a patient is described, comprising: modifying the refractive index of ocular tissue of an eye of the patient, by irradiating select regions of the ocular tissue with a focused, visible or near-IR laser below the optical breakdown threshold of the tissue to provide refractive structures that exhibit a change in refractive index, and exhibit little or no scattering loss, and scanning over the select regions with the laser such that ablation or removal of the tissue is not observed in the irradiated region, wherein the refractive structures are formed while the ocular tissue is in a curved, relatively low-internal stress form to reduce distortions of the refractive structures or of the shape of the ocular tissue which result when the structures are formed while the ocular tissue is in a stressed applanated form. Further, the refractive structures preferably cover the majority of area of a circular zone of 6 mm diameter, so as to cover the majority of the clinically relevant optical zone of the eye. Such refractive structures may further preferably be written in the form of a Fresnel lens, so as to enable greater diopter changes.

In a further embodiment, method for modifying visual performance in a patient is described, comprising: modifying the refractive index of ocular tissue of an eye of the patient, by irradiating select regions of the ocular tissue with a focused, visible or near-IR laser below the optical breakdown threshold of the tissue to provide refractive structures that exhibit a change in refractive index, and exhibit little or no scattering loss, and scanning over the select regions with the laser such that ablation or removal of the tissue is not observed in the irradiated region, wherein the refractive structures are formed in a pattern while the ocular tissue is in a stressed applanated form, where removal of the stress results in a change of the pattern or of the shape of the ocular tissue, and wherein the pattern written while the ocular tissue is in a stressed applanated form is designed to result in a desired pattern and/or shape of the ocular tissue upon removal of the stress. Further, the refractive structures preferably cover the majority of area of a circular zone of 6 mm diameter, so as to cover the majority of the clinically relevant optical zone of the eye. Such refractive structures may further preferably be written in the form of a Fresnel lens, so as to enable greater diopter changes.

In a further embodiment, a method for modifying visual performance in a patient, comprising: modifying the refractive index of ocular tissue of an eye of the patient, by irradiating select regions of the ocular tissue with a focused, visible or near-IR laser below the optical breakdown threshold of the tissue to provide refractive structures that exhibit a change in refractive index, and exhibit little or no scattering loss, and scanning over the select regions with the laser such that ablation or removal of the tissue is not observed in the irradiated region, wherein the refractive structures are formed in a pattern which results in an overall shape change to the ocular tissue, and wherein the shape change is employed in combination with the refractive index change to provide a desired optical correction for the ocular tissue. The shape change may be dynamic resulting in gradual prescription changes over time, and the gradual prescription change of the ocular tissue may be designed to provide a gradual change to a target prescription. Further, the refractive structures preferably cover the majority of area of a circular zone of 6 mm diameter, so as to cover the majority of the clinically relevant optical zone of the eye. Such refractive structures may further preferably be written in the form of a Fresnel lens, so as to enable greater diopter changes. Where the ocular surface comprises the cornea, the refractive structures may be formed in a pattern which results in a decrease or increase in the cornea anterior surface radius of curvature.

In each of the described embodiments, the refractive structures may preferably comprise a refractive index GRIN layer, and more particularly where the refractive structures cover the majority of area of a circular zone of 6 mm diameter, so as to cover the majority of the clinically relevant optical zone of the eye. Such refractive structures may further preferably be written in the form of a Fresnel lens, so as to enable greater diopter changes.

While specific embodiment have been set forth in detail above, those skilled in the art who have reviewed the present disclosure will readily appreciate that other embodiments can be realized within the scope of the invention. For example, numerical values are illustrative rather than limiting, as are recitations of specific equipment and sources. While embodiments have been disclosed in terms of two-photon absorption, such embodiments can be implemented similarly through absorption of three or more photons. Therefore, the present invention should be construed as limited only by the appended claims.

We claim:

1. A method for modifying visual performance in a patient, comprising:
   identifying a desired optical vision correction to be achieved in an eye of the patient,
   modifying the refractive index of select regions of ocular tissue of the eye of the patient, by irradiating the select regions of the ocular tissue with a focused, visible or near-IR laser below the optical breakdown threshold of the ocular tissue to provide refractive structures that exhibit a change in refractive index, and exhibit little or no scattering loss, and scanning over the select regions with the laser such that ablation or removal of the ocular tissue is unobservable in the irradiated region,
   wherein the refractive structures are designed to include refractive structures formed in a pattern which results in an overall shape change to the ocular tissue, and wherein vision change resulting from the overall shape change is employed in combination with refractive index changes in the refractive structures to provide the identified desired optical vision correction to be achieved in the eye of the patient.

2. A method according to claim 1, wherein the refractive structures cover the majority of area of a circular zone of 6 mm diameter.

3. A method according to claim 1, wherein the refractive structures include refractive structures written in the form of a Fresnel lens or a diffractive pattern.

4. A method according to claim 1, wherein the ocular tissue comprises the cornea, and the refractive structures are formed in a pattern which results in a decrease or increase in a cornea anterior surface radius of curvature.

5. A method according to claim 1, wherein the ocular tissue comprises the cornea, and the refractive structures are formed in a pattern which results in an annular region of the cornea having a flattened anterior surface curvature.

6. A method according to claim 1, wherein the ocular tissue comprises the cornea, and the refractive structures are formed in a pattern which results in a decrease in curvature of an anterior surface in a treated area of the cornea.

7. A method according to claim 6, wherein a wavefront pattern is written in the cornea over all or the majority of a treated optical zone in order to induce a desired degree of thickness change and optical power associated with such thickness change over the treated optical zone.

8. A method according to claim 1, wherein the ocular tissue comprises the cornea, and wherein one or more shape change layers designed to primarily effect a desired shape change is written at a first depth relative to an anterior surface of the cornea, where such written one or more shape change layer written at the first depth relative to the anterior surface of the cornea will have a greater effect on shape change than if written at a depth further from the anterior surface of the cornea, and one or more additional layer with patterns designed to provide primarily refractive index change features is written at a second depth relatively further than the first depth from the anterior surface of the cornea, where the combination of shape change from the one or more shape change layer written at the first depth relative to the anterior surface of the cornea and the refractive index changes from the one or more additional layer written at the second depth relatively further than the first depth from the anterior surface of the cornea in combination provide a desired optical correction.

9. A method according to claim 8, wherein the one or more shape change layer is written within 250 microns of the anterior surface of the cornea.

10. A method according to claim 8, wherein the shape change provides a spherical correction, and the refractive index changes correct for astigmatism or higher order aberrations.

11. A method according to claim 8, wherein the shape change correction provides a sphere or cylinder correction, and the refractive index changes provide a multifocal or extended depth of focus correction.

12. A method according to claim 8, wherein the one or more additional layer comprises one or more GRIN layers and/or Fresnel lens layers designed to provide tailored aberration corrections.

13. A method according to claim 1, wherein the shape change is dynamic resulting in gradual prescription changes over time.

14. A method according to claim 13, wherein the gradual prescription change of the ocular tissue is designed to provide a gradual change to a target prescription.

15. A method according to claim 1, wherein the refractive structures comprise a refractive index GRIN layer.

16. A method according to claim 15, wherein the refractive structures cover the majority of area of a circular zone of 6 mm diameter.

17. A method according to claim 15, wherein the refractive structures are written in the form of a Fresnel lens.

18. A method according to claim 1, wherein the ocular tissue comprises the cornea, and the laser has a wavelength is from 400 to 1300 nm, Numerical Aperture is 0.1 to 1.1, pulse-width is from 10-1000 fs, repetition rate is from 1-100 MHz, laser scan line spacing is from 0.01 to 100 um, scan speed is from 10 to 10,000 mm/sec, laser power is from 10 to 10,000 mW, the refractive structures are written over an optical zone diameter of from 1-10 mm, from 1-10 layers of refractive index structures are written with axial separation of from 0 to 100 um, and each written layer thickness is from 1 to 100 um.

19. A method for modifying visual performance in a patient, comprising:

modifying the refractive index of ocular tissue of an eye of the patient, by irradiating select regions of the ocular tissue with a focused, visible or near-IR laser below the optical breakdown threshold of the ocular tissue to provide refractive structures that exhibit a change in refractive index, and exhibit little or no scattering loss, and scanning over the select regions with the laser such that ablation or removal of the ocular tissue is unobservable in the irradiated region, wherein the refractive structures are formed in a pattern while the ocular tissue is in a stressed applanated form, where removal of the stress results in a change of the pattern or of the shape of the ocular tissue, and wherein the pattern written while the ocular tissue is in a stressed applanated form is designed to result in a desired pattern or shape of the ocular tissue upon removal of the stress.

20. A method according to claim 19, wherein the refractive structures cover the majority of area of a circular zone of 6 mm diameter.

21. A method according to claim 19, wherein the refractive structures are written in the form of a Fresnel lens.

22. A method according to claim 19, wherein the refractive structures comprise a refractive index GRIN layer.

* * * * *